US008945518B2

(12) United States Patent
Jia et al.

(10) Patent No.: US 8,945,518 B2
(45) Date of Patent: Feb. 3, 2015

(54) FORMULATION OF DUAL EICOSANOID SYSTEM AND CYTOKINE SYSTEM INHIBITORS FOR USE IN THE PREVENTION AND TREATMENT OF ORAL DISEASES AND CONDITIONS

(75) Inventors: Qi Jia, Olympia, WA (US); Yuan Zhao, Olympia, WA (US)

(73) Assignee: Unigen, Inc., Seattle, WA (US)

( * ) Notice: Subject to any disclaimer, the term of this patent is extended or adjusted under 35 U.S.C. 154(b) by 1257 days.

(21) Appl. No.: 11/254,433

(22) Filed: Oct. 19, 2005

(65) Prior Publication Data

US 2006/0079467 A1    Apr. 13, 2006

Related U.S. Application Data

(63) Continuation-in-part of application No. 10/427,746, filed on Apr. 30, 2003, now Pat. No. 7,514,469, which is a continuation-in-part of application No. 10/462,030, filed on Jun. 13, 2003, now Pat. No.

(Continued)

(51) Int. Cl.
*A61K 8/66* (2006.01)
*A61K 8/96* (2006.01)
(Continued)

(52) U.S. Cl.
CPC ............... *A61K 31/353* (2013.01); *A61K 8/97* (2013.01); *A61Q 11/00* (2013.01); *A61K 31/7048* (2013.01)
USPC .......................................................... 424/50

(58) Field of Classification Search
CPC ................................................... A61Q 11/00
USPC ............................................................ 424/50
See application file for complete search history.

(56) References Cited

U.S. PATENT DOCUMENTS 3,686,872 A    8/1972    Whitworth et al.
3,706,581 A    12/1972   Whitworth et al.

(Continued)

FOREIGN PATENT DOCUMENTS

CA    2 484 192 A1    11/2003
CN    1093914         10/1994

(Continued)

OTHER PUBLICATIONS

Tsao et al (Journal of Dental Research 61 (9): (1982) 1103).*

(Continued)

*Primary Examiner* — Benjamin Packard
(74) *Attorney, Agent, or Firm* — Seed IP Law Group PLLC

(57) ABSTRACT

The present invention provides a novel composition of matter comprised of a mixture of two specific classes of compounds—Free-B-Ring flavonoids and flavans—for use in the prevention and treatment of diseases and conditions associated with mouth, gums and teeth. This composition of matter simultaneously inhibits cyclooxygenase (COX) and lipoxygenase (LOX) enzymatic activity and reduces cytokine production at the mRNA level in normal, aged and damaged periodontal cells and tissues. This invention further provides a method for the prevention and treatment of diseases and conditions of the mouth, gums and teeth. The method for preventing and treating diseases and conditions of the mouth, teeth and gums is comprised of administering to a host in need thereof a therapeutically effective amount of a composition comprising a mixture of Free-B-Ring flavonoids and flavans synthesized and/or isolated from a single plant or multiple plants, preferably in the *Scutellaria, Oroxylum, Acacia* or *Uncaria* genus of plants and pharmaceutically and/or cosmetically acceptable carriers. Finally the present invention provides a method for the prevention and treatment of diseases and conditions of the mouth, teeth or gums, including but not limited to periodontal diseases, such as gingivitis, periodontitis, pulpitis, periodontal conditions caused by the physical implantation of oral dentures, trauma, injuries, bruxism, neoplastic and other degenerative processes; material alba, pellicles, dental plagues, calculus, and stains. Use of the composition described herein also affords the benefit of maintaining optimum saliva production and pH, minimizing bacterial growth, reducing the formation of pellicles and plague, inhibiting tooth decalcification and tooth caries (decay), promoting remineralization, which yields healthy gums, whitening teeth, maintaining healthy oral hygiene and reducing oral malodor (halitosis).

11 Claims, 11 Drawing Sheets

Related U.S. Application Data 7,674,830, and a continuation-in-part of application No. 10/785,704, filed on Feb. 24, 2004, now Pat. No. 7,531,521, application No. 11/254,433, which is a continuation-in-part of application No. 10/932,571, filed on Sep. 1, 2004, now abandoned.

(60) Provisional application No. 60/620,163, filed on Oct. 19, 2004, provisional application No. 60/377,168, filed on Apr. 30, 2002, provisional application No. 60/450,922, filed on Feb. 26, 2003, provisional application No. 60/499,742, filed on Sep. 2, 2003.

(51) Int. Cl.
  *A61Q 11/00* (2006.01)
  *A61K 31/353* (2006.01)
  *A61K 8/97* (2006.01)
  *A61K 31/7048* (2006.01)

(56) References Cited

U.S. PATENT DOCUMENTS

| | | | |
|---|---|---|---|
| 4,268,517 A | | 5/1981 | Niebes et al. |
| 4,374,824 A | | 2/1983 | Wahmi |
| 4,515,804 A | | 5/1985 | Marti et al. |
| 5,156,835 A | * | 10/1992 | Nabi et al. ............... 426/52 |
| 5,437,856 A | | 8/1995 | Lukacovic et al. |
| 5,470,589 A | | 11/1995 | Shi |
| 5,589,160 A | * | 12/1996 | Rice ............... 424/49 |
| 5,605,929 A | | 2/1997 | Liao et al. |
| 5,643,598 A | | 7/1997 | Maybeck |
| 5,650,432 A | * | 7/1997 | Walker et al. ............... 514/456 |
| 5,756,538 A | | 5/1998 | Cassels et al. |
| 5,795,911 A | | 8/1998 | Cheng et al. |
| 5,804,168 A | | 9/1998 | Murad |
| 5,858,371 A | | 1/1999 | Singh et al. |
| 5,886,029 A | | 3/1999 | Dhaliwal |
| 5,922,756 A | | 7/1999 | Chan |
| 5,962,517 A | | 10/1999 | Murad |
| 5,968,973 A | | 10/1999 | Cheng et al. |
| 6,080,401 A | | 6/2000 | Reddy et al. |
| 6,083,921 A | | 7/2000 | Xu |
| 6,093,403 A | | 7/2000 | Huo et al. |
| 6,126,940 A | | 10/2000 | Takahashi et al. |
| 6,126,950 A | | 10/2000 | Bindra et al. |
| 6,197,808 B1 | | 3/2001 | Cheng et al. |
| 6,217,875 B1 | | 4/2001 | Murai et al. |
| 6,221,341 B1 | | 4/2001 | Montgomery |
| 6,235,294 B1 | | 5/2001 | Perrier et al. |
| 6,248,341 B1 | | 6/2001 | Anderson et al. |
| 6,264,926 B1 | | 7/2001 | Farooqi |
| 6,264,995 B1 | | 7/2001 | Newmark et al. |
| 6,280,751 B1 | | 8/2001 | Fletcher et al. |
| 6,290,995 B1 | | 9/2001 | Xinxian |
| 6,319,523 B1 | | 11/2001 | Zhou |
| 6,333,304 B1 | | 12/2001 | Bath et al. |
| 6,387,416 B1 | | 5/2002 | Newmark et al. |
| 6,391,346 B1 | | 5/2002 | Newmark et al. |
| 6,475,530 B1 | | 11/2002 | Kuhrts |
| 6,555,573 B2 | | 4/2003 | Rosenbloom |
| 7,045,158 B2 | | 5/2006 | Wolfson et al. |
| 7,108,868 B2 | | 9/2006 | Jia et al. |
| 7,189,385 B2 | | 3/2007 | Montgomery |
| 7,514,469 B2 | | 4/2009 | Jia |
| 7,531,521 B2 | | 5/2009 | Burnett et al. |
| 7,674,830 B2 | | 3/2010 | Jia |
| 7,695,743 B2 | | 4/2010 | Jia et al. |
| 7,972,632 B2 | | 7/2011 | Jia |
| 8,034,387 B2 | | 10/2011 | Jia et al. |
| 8,124,134 B2 | | 2/2012 | Jia et al. |
| 8,535,735 B2 | | 9/2013 | Jia et al. |
| 8,568,799 B2 | | 10/2013 | Jia et al. |
| 2002/0086070 A1 | | 7/2002 | Kuhrts |
| 2002/0122836 A1 | | 9/2002 | Obukowicz et al. |
| 2002/0136784 A1 | | 9/2002 | Obukowicz et al. |
| 2003/0105030 A1 | | 6/2003 | Liao et al. |
| 2003/0113797 A1 | | 6/2003 | Jia et al. |
| 2003/0125264 A1 | | 7/2003 | Malik |
| 2003/0165588 A1 | | 9/2003 | Jia et al. |
| 2003/0216481 A1 | | 11/2003 | Jia et al. |
| 2004/0057908 A1 | | 3/2004 | Bowen et al. |
| 2004/0186062 A1 | * | 9/2004 | Burnett et al. ............... 514/27 |
| 2004/0220119 A1 | | 11/2004 | Jia |
| 2006/0140881 A1 | | 6/2006 | Xu et al. |
| 2006/0141073 A1 | | 6/2006 | Worrell et al. |
| 2006/0177528 A1 | | 8/2006 | Jia |
| 2006/0204596 A1 | | 9/2006 | Jia et al. |
| 2008/0096826 A1 | | 4/2008 | Jia |
| 2011/0207806 A1 | | 8/2011 | Jia |

FOREIGN PATENT DOCUMENTS

| | | | |
|---|---|---|---|
| CN | 1096680 A | | 12/1994 |
| CN | 1043406 C | | 5/1999 |
| CN | 1285202 A | | 2/2001 |
| EP | 633022 B | | 2/1997 |
| EP | 0956867 A1 | | 11/1999 |
| FR | 2651132 | | 3/1991 |
| GB | 2 024 817 A | | 1/1980 |
| GB | 2 306 321 A | | 5/1997 |
| JP | 61050921 | | 3/1986 |
| JP | 64-90124 A | | 4/1989 |
| JP | 403240725 | | 10/1991 |
| JP | 07-017847 A | | 1/1995 |
| JP | 07010768 | | 1/1995 |
| JP | 7-55895 B2 | | 6/1995 |
| JP | 07-165598 A | | 6/1995 |
| JP | 07 223941 | | 8/1995 |
| JP | 07-242555 A | | 9/1995 |
| JP | 07242555 | | 9/1995 |
| JP | 8104628 A | | 4/1996 |
| JP | H08-104628 A | | 4/1996 |
| JP | 10-025238 A | | 1/1998 |
| JP | 63027435 | | 2/1998 |
| JP | 10130162 | | 5/1998 |
| JP | 2002053484 | | 2/2002 |
| JP | 2003 212771 | | 7/2003 |
| JP | 2004 244385 | | 9/2004 |
| JP | 2004-244385 A | | 9/2004 |
| JP | 2005-519100 A | | 6/2005 |
| KR | 1996-0003725 A | | 2/1996 |
| WO | WO 97/36497 | | 10/1997 |
| WO | WO 98/19651 | | 5/1998 |
| WO | 98/40086 A2 | | 9/1998 |
| WO | WO 98/42363 | | 10/1998 |
| WO | WO 98/49256 | | 11/1998 |
| WO | WO0059523 | * | 10/2000 ............... A61K 35/78 |
| WO | 02/07745 A1 | | 1/2002 |
| WO | WO 02/09699 | | 2/2002 |
| WO | WO 02/47615 | | 6/2002 |
| WO | 03/002134 A1 | | 1/2003 |
| WO | 03/024470 A1 | | 3/2003 |
| WO | 03/074065 A1 | | 9/2003 |
| WO | 03/082312 A1 | | 10/2003 |
| WO | 03/092599 | | 11/2003 |
| WO | WO 03/092599 | | 11/2003 |
| WO | 2004/058279 A1 | | 7/2004 |
| WO | 2005/020932 | | 3/2005 |
| WO | 2006/099217 A2 | | 9/2006 |

OTHER PUBLICATIONS

Asaki et al (Journal of the Japanese Association of Periodontology, 37:2 (1995) 412-421, English Abstract only).*
Afolayan and Meyer (1997) Journal of Ethnopharmacol. 57(3):177-181.
Agarwal et al. (Nov. 1993) Photochem. Photobiol. 58:695-700.
Amos et al. (1999) Phytotherapy Research 13:683-685.
Bastianetto et al. (2000) Br. J. Pharmacol. 131:711-720.
Boumendjel et al. (2001) Bioorg. Med. Chem. Lett. 11(1):75-77.
Butenko et al. (1993) Agents Actions Special Conference Issue 39:C49-C51.

(56) References Cited

OTHER PUBLICATIONS

Chen et al. (2001) Biochem. Pharmacol. 61(11):1417-1427.
Chi et al. (2001) Biochem. Pharmacol. 61:1195-1203.
Commenges et al. (Apr. 2000) Eur. J. Epidemiol 16:357-363.
Dafallah and Al-Mustafa (1996) American Journal of Chinese Medicine. 24:263-269 (Abstract only).
Genco et al. (1990) in *Contenporary Periodontics*, The C.V. Mosby Company, St. Louis, pp. 361-370.
Gilani et al. (Dec. 1999) Phytotherapy Research. 13:665-669.
Hagos et al. (Feb. 1987) Planta Medica. 53:27-31.
Hanausek-Walaszek et al. (Mar. 2000) Proceedings American Association for Cancer Research Annual Meeting 41:663 (abstract #4216).
Haridas et al. (Mar. 2000) Proceedings American Association for Cancer Research Annual Meeting. 41:600 (abstract #3820).
Heo et al. (2001) Mutat. Res. 488(2):135-150.
Hong et al. (2001) Biochem. Pharmacol. 62:1175-1183.
Imamura et al. (2000) J. Biochem. 127(4):653-658.
Itoigawa et al. (1999) J. Ethnopharmacol. 65(3): 267-272.
Kalkbrenner et al. (1992) Pharmacology 44(1):1-12.
Kaneko and Baba (1999) Biosci Biotechnol. Biochem 63(2):323-328.
Kikukawa et al. (1995) Ensho 15(2):129-33 (English Abstract).
Kim et al. (1990) Yakhak Hoeji 34(5):348-364.
Kimura et al. (2001) Planta Med. 67:331-334.
Krakauer et al. (2001) FEBS Lett. 500:52-55.
Kubo et al. (1984) Chemical and Pharmaceutical Bulletin 32(7):2724-2729.
Kubo et al. (2000) Bioorg. Med. Chem. 8(7):1749-1755.
Li et al. (2000) Immunopharmacology 49:295-306.
Liang et al. (2001) FEBS Lett. 496(1):12-18.
Meyer et al. (1997) J. Ethnopharmacol. 56(2):165-169.
Min et al. (1999) Planta Med. 65:460-462.
Moroney et al. (1988) J. Pharm. Pharmacol. 40:787-792.
Mutoh et al. (Jul. 2000) Jnp. J. Cancer Res. 91:686-691.
Nadkarni (1996) India Materia Medica, Bombay Popular Prakashan, pp. 9-17.
Nakahata et al. (1998) Am. J. Chin Med. 26:311-323.
Nakahata et al. (1999) Nippon Yakurigaku Zasshi 114, Supp. 11 :215P-219P (Eng. abstract).
Nakajima et al. (2001) Planta Med. 67(2):132-135.
Noreen et al. (1998) Planta Med. 64:520-524.
Noreen et al. (Jan. 1998) J. Nat. Prod. 61:2-7.
Noreen et al. (Jan. 1998) J. Nat. Prod. 61:8-12.
Park et al. (2001) Biochem. Biophys. Res. Commun. 286:721-725.
de la Puerta et al. (1999) Planta Medica 65:507-511.
Raso et al. (2001) Life Sci. 68(8):921-931.
Shah et al. (1997) General Pharmacology. 29:251-255.
So et al. (1997) Cancer Lett. 112(2):127-133.
Sobottka et al. (2000) Arch. Pharm. Pharm. Med. Chem. 333:205-210.
Tordera et al. (Mar.-Apr. 1994) Z. Naturforsch [C] 49:235-240.
de Whalley et al. (1990) Biochemical Pharmacology 39:1743-1750.
Wakabayashi and Yasui (2000) Eur. J. Pharmacol. 406(3):477-481.
Wang (Mar. 2000) Phytomedicine 7:15-19.
Wenzel et al. (Jul. 2000) Cancer Res. 60:3823-3831.
Yamahara et al. (1981) Shoyakugaku Zasshi 35(2):103-107 (English Abstract).
Yang et al. (1999) J. Nutr. Sci. Vitaminol. 45:337-346.
You et al. (1999) Arch. Pharm. Res. 22:18-24.
Chen et al., Oroxylin A inhibition of lipopolysaccharide-induced iNOS and COX-2 gene expression via suppression of nuclear factor-kappaB activation (Jun. 1, 2000) Biochemical Pharmacology 59:1445-1447.
Chung et al., Pharmacological Effects of Methanolic Extract from the Root of *Scutellaria baicalensis* and its Flavonoids on Human Gingival Fibroblast (Apr. 1995) Planta Med. 61:150-153.
Exotic naturals, 2007, 2 pages "*Acacia catechu* extract", http:/www.exotocnatural.com/acacia-catechu.htm.
Nakagami (Aug. 22, 1995) abstract Database WPI Week 199519 Aug. 22, 1995, Derwent Publications Ltd., London, GB; p. 2, AN 1995-325471 XP002418722 Nakagami T; Nakamura T; Tamura N: "Anti-complementary substance used as therapeutic agent—comprises gallic acid, methyl gallate, acetyl-salicylic acid, caffeic acid, catechin, epi-gallo-catechin gallate, myricetin, quercitrin and/or baicalein, or their salts" & JP 07 223941 A ((NIHA-N) Nippon Ham KK), Abstract only.
Chung et al. (Apr. 1, 1995) Planta Medica 61(2):150-153, "Pharmacological Effects of Methanolic Extract from the Root of *Scutellatia baicalensis* and Its Flavonoids of Human gingival Fibroblast".
Li, Ji-yao, (Jan. 1, 1990) Medline, "The effect of Radix *Scutellaria* on *Porphyromonas* endodantalis in vitro".
2004 International Congress on Natural Products Research, Phoenix, Arizona, Jul. 31-Aug. 4, 2004, Gafner et al., Evaluation of the anti-inflammatory properties of skullcap (*Scutellaria lateriflora* L.) extracts in different in vitro models, P:60 and poster.
Xiaozhen (Oct. 2002) Medical Journal of Wuhan University 23(4):301-305, "Induction of PGE2 Production and COX-2 Expression in Human Gingival Fibroblasts Stimulated with LPS", Englsih Abstract only.
Ali Ibn-e-Abbaas Majoosi; Kaamil-al-Sena'ah, Part II Kaamil-al-Sena'ah, Part II (10th century AD), Central Council for Research in Unani Medicine, 61-65 Institutional Area, Janak Puri, New Delhi-58, 2005 AD p. 129, Formulation ID: AH3/876C, Formulation Name: Zimaad Baraae, Qooba, 3 pages (English translation).
Bhāvamiśra; Bhāvaprakāśa—Edited & translated by Brahmashankara Misra & RupaLalaji Vaisya, Part-I: Chaukhambha Sanskrit Sansthan, Varanasi, Edn. 9th, 1999, Time of origin 16th century, p. 110, Formulation ID: RS/3007D, Formulation Name: Dantakūrcikā (04), 3 pages (English translation).
Qi Jia et al., "Flavonoid Composition for Treating Oral Diseases," Third Party Observation dated May 30, 2011, for EP Application No. 05810437.3, 42 pages.
Mohammad Akmal Khan, Qaraabaadeen Azam wa Akmal (20th century AD), Matba Siddiqi, Delhi/Matba Mustafai, Delhi, 1909 AD p. 410, Formulation ID: AH5/610, Formulation Name: Sanoon Bara-e-Zirs, 3 pages (English translation).
Mohammad Akmal Khan, Qaraabaadeen Azam wa Akmal (20th century AD), Matba Siddiqi, Delhi/Matba Mustafai, Delhi, 1909 AD p. 173, Formulation ID: BA3/1032, Formulation Name: Nuskha Sanoon, 3 pages. (English translation).
Mohammad Najmul Ghani Khan; Qaraabaadeen Najm-al-Ghani (20th century AD), Munshi Nawal Kishore, Lucknow, (Second Edition), 1928 AD p. 667, Formulation ID: NA4/4357, Formulation Name: Manjan Deegar, 3 pages (English translation).
Sodhala; Gadanigrahah ed, Ganga Sahaya Pandeya & Com., Indradeva Tripathi, Part-3(Salakya-Pancakarma Khanda) Chaukhamba Sanskrit Sansthan(Varanasi) Ed. 3rd 1999, p. 225, Formulation ID: RG2/525, Formulation Name: Dantasula Cikitsa, 3 pages (English translation).
Sodhala; Gadanigrahah ed, Ganga Sahaya Pandeya & Com., Indradeva Tripathi, Part-1(prayoga Khanda) Chaukhamba Sanskrit Sansthan, Varanasi, Ed. 3rd 1999, p. 107-108, Formulation ID: AK2/158, Formulation Name: Khadiradyam Tailam, 6 pages. (English translation).
Vāgbhata; Astānga Sarngraha—(commentary by Indu), Part-I(KA); Central Council for Research in Ayurveda & Siddha, New Delhi, 1991, Time of origin 5-10th century, p. 27, Formulation ID: AT/2103, Formulation Name: Gandūsadhāranādigunaāh, 3 pages (English translation).
WPI/Thomson Database, Accession No. 1989-147372 [20], "Compsns. acting on dental caries and periodontosis—contain polyphenol cpds. pref. obtd. from tea by extn. with water," 1989, 1 page.
Elattar et al., "Hydoxy fatty acids and prostaglandin formation in diseased human periodontal pocket tissue," *Journal of Periodontal Research* 21:169-176, 1986.
Gaffar et al., "The effect of triclosan on mediators of gingival inflammation," *J. Clin. Periodontal.* 22:480-484, 1995.

(56) References Cited

OTHER PUBLICATIONS

Li et al., "Chemoprevention of 7,12-dimethylbenz[a]anthracene (DMBA)-induced oral carcinogenesis in hamster cheek pouch by a cyclooxygenase 2 inhibitor (Celecoxib) and a 5-lipoxygenase inhibitor (Zileuton)," *AACR Meeting Abstracts*, Abstract No. 546-a, 2004.

Oringer, "Modulation of the Host Response in Periodontal Therapy," *J. Periodontal.* 73:460-470, 2002.

"*Scutellaria* Root / *Official Monographs for Part II*", JP XIV, The Japanese Pharmacopoeia, Fourteenth Edition, English Version, Society of Japanese Pharmacopoeia, Tokyo, Japan, 2001, pp. 1042-1043.

Abdulrazak et al., "Chemical Composition, Phenolic Concentration and In Vitro Gas Production Characteristics of Selected Acacia Fruits and Leaves," *Asian-Aus J Anim Sci 13*(7):935-940, 2000.

Gupta, Third Party Submission, dated Feb. 15, 2013; received in USPTO Feb. 25, 2013. (3 pages).

Gupta, V. K., Senior Advisor and Director, TKDL, Third Party Observations, dated Sep. 10, 2010, in Canadian Application No. 2,584,124; received in CIPO Sep. 30, 2010, 7 pages.

Gupta, V. K., Senior Advisor and Director, TKDL, Third Party Observation, dated Feb. 7, 2011, in Canadian Application No. 2,521,429; received in CIPO Feb. 15, 2011, 8 pages.

Gupta, V. K., Senior Advisor and Director, TKDL, Third Party Observation, dated Apr. 26, 2011, in European Application No. 05810437.3; received in EPO May 9, 2011, 7 pages.

Lee et al., "Pharmacokinetics of Tea Catechins after Ingestion of Green Tea and (—)-Epigallocatechin-3-gallate by Humans: Formation of Different Metabolites and Individual Variability," *Cancer Epidemiol, Biomarkers & Prev 11*:1025-1032, Oct. 2002.

Saleem et al., "Chemistry of the Medicinal Plants of Genus *Acacia*," *Hamard Medicus XLI*(1):63-67, 1998.

Vautrin, "Etude botanique, chimique et pharmacologique du genre acacia. (Botanical, Chemical and Pharmacological study of the *Acacia* species)," D. Pharm, *Université de Dijon* (France), pp. 94, 1996.

Woodall et al., "Preventing Periodontal Disease," *Preventive Periodontics*, The C.V. Mosby Company St. Louis, 361-370, 1990.

Gupta, V.K., Senior Advisor and Director, TKDL, Third Party Observations filed Oct. 9, 2010 in CA 02584125.

\* cited by examiner

FORMULATION OF DUAL EICOSANOID SYSTEM AND CYTOKINE SYSTEM INHIBITORS FOR USE IN THE PREVENTION AND TREATMENT OF ORAL DISEASES AND CONDITIONS

RELATED APPLICATIONS

This application claims the benefit of U.S. Provisional Application Ser. No. 60/620,163, filed Oct. 19, 2004, entitled "Formulation of Dual Cycloxygenase (COX) and Lipoxygenase (LOX) Inhibitors for Use in the Prevention and Treatment of Oral Diseases and Conditions." This application is also a Continuation in Part of U.S. application Ser. No. 10/427,746, filed Apr. 30, 2003, which claims the benefit of U.S. Provisional Application Ser. No. 60/377,168, filed Apr. 30, 2002, each of which is entitled "Formulation of a Mixture of Free-B-Ring Flavonoids and Flavans as a Therapeutic Agent;" U.S. application Ser. No. 10/462,030, filed Jun. 13, 2003, entitled entitled "Formulation of a Mixture of Free-B-Ring Flavonoids and Flavans as a Therapeutic Agent;" U.S. application Ser. No. 10/785,704, filed Feb. 24, 2004, which claims the benefit of U.S. Provisional Application Ser. No. 60/450,922, filed Feb. 26, 2003, each of which is entitled "Formulation for Use in the Prevention and Treatment of Carbohydrate Induced Diseases and Conditions;" and U.S. application Ser. No. 10/932,571, filed Sep. 1, 2004, which claims the benefit of U.S. Provisional Application Ser. No. 60/499,742, filed Sep. 2, 2003, each of which is entitled "Formulation of a Mixture of Free-B-Ring Flavonoids and Flavans for Use in the Prevention and Treatment of Cognitive Decline and Age-Related Memory Impairments." Each of these applications is incorporated herein by reference in its entirety.

FIELD OF THE INVENTION

This invention relates generally to a novel composition of matter comprised of a mixture of a blend of two specific classes of compounds—Free-B-Ring flavonoids and flavans—which target the eicosanoid and cytokine pathways for use in the prevention and treatment of diseases and conditions of the mouth, teeth and gums. Specifically, the diseases and conditions of the mouth, teeth and gums include but not limited to periodontal diseases, such as gingivitis, periodontitis, pulpitis, periodontal conditions caused by the physical implantation of oral dentures, trauma, injuries, bruxism, neoplastic and other degenerative processes; material alba, pellicles, dental plagues, calculus, and stains. Use of the composition described herein also affords the benefit of maintaining optimum saliva production and pH, minimizing bacterial growth, reducing the formation of pellicles and plague, inhibiting tooth decalcification and tooth caries (decay), promoting remineralization, yielding healthy gums, whitening teeth, maintaining healthy oral hygiene and reducing oral malodour (halitosis).

BACKGROUND OF THE INVENTION

Periodontal disease is a combination of inflammation and infection of some or all of the tooth support structures (gingiva, cementum, periodontal ligament, alveolar bone and other tissues surrounding the teeth). Gingivitis (gums) and periodontitis (gums and bone) are the two main forms of periodontal disease. According to National Oral Information distributed by the National Institute of Dental and Craniofacial Research, an estimated 80 percent of American adults currently have some form of periodontal disease. Periodontal disease is initiated when a pellicle forms on a clean tooth or teeth. This pellicle attracts aerobic gram-positive bacteria (mostly actinomyces and streptococci), which adhere to the tooth forming plaque. Within days the plaque thickens, the underlying bacteria run out of oxygen and anaerobic motile rods and spirochetes begin to populate the subgingival area. Endotoxins released by the anaerobic bacteria cause inflammation, gum tissue destruction and even bone loss. There are four primary stages of periodontal disease that can be characterized as indicated below. The destructive impact of periodontal disease goes beyond dental hygiene and health, in that microscopic lesions resulting from periodontal disease have been found in the liver, kidneys, and brain of some affected persons.

| Four Stages of Periodontal Disease |
| --- |
| Grade 1 Inflammation |
| Grade 2 Inflammation, edema, gingival bleeding upon probing |
| Grade 3 Inflammation, edema, gingival bleeding upon probing, pustular discharge - slight to moderate bone loss |
| Grade 4 Inflammation, edema, gingival bleeding upon probing, pustular discharge, mobility - severe bone loss |

The inflammation resulting from periodontal disease is mainly related to two biological systems:—the eicosanoid system and the cytokine system. The release and metabolism of arachidonic acid (AA) from the cell membrane results in the generation of pro-inflammatory metabolites by several different pathways. Two of the most important pathways to inflammation are mediated by the enzymes lipoxygenase (LOX) and cyclooxygenase (COX). These are parallel pathways that result in the generation of leukotrienes and prostaglandins, respectively, which play important roles in the initiation and progression of the inflammatory response. These vasoactive compounds are chemotaxins, which both promote infiltration of inflammatory cells into gum tissue and serve to prolong the inflammatory response that may lead to bone loss. Consequently, the enzymes responsible for generating these mediators of inflammation can be targeted to develop therapeutic agents to prevent and treat diseases and conditions related to the mouth, teeth and gums.

The cytokine system is a very potent force in homeostasis when activation of the network is local and the cytokines act vicinally in surface-bound or diffusible form. But when cytokine production is sustained and/or systemic, cytokines contribute to the signs, symptoms, and pathology of inflammatory, infectious, autoimmune, and malignant diseases. TNF-α is a potent pleiotropic cytokine produced by macrophages, neutrophiles, fibroblasts, keratinocytes, NK cells T and B cell and tumor cells. IL-1β, together with TNF-α, plays a central role in inflammatory responses. Administration of antagonists, such as IL-1ra (IL-1 receptor antagonist), soluble fragment of IL-1 receptor, or monoclonal antibodies to TNF-α and soluble TNF receptor, all block various acute and chronic responses in animal models of inflammatory diseases. Nuclear factor kappa B (NFκB) is a transcription factor that controls gene expression of interleukin-1 beta (IL-1β), tumor necrosis factor-alpha (TNFα), interleukin-6 (IL-6) and many other proteins. Some of these antagonists are beginning to be utilized as anti-inflammatory agents in diseases such as sepsis, periodontal diseases and rheumatoid arthritis. (Dinarello (2004) Curr Opin Pharmacol. 4:378-385). Anti-TNF-α antibodies were not only found to induce striking remissions in rheumatoid arthritis, but also to reduce tissue inflammation in Crohn's disease, an inflammatory bowel disease (Maini and Feldmann. (2002) Arthritis Res. 4 Suppl 2: S22-8).

Periodontal ligament (PDL) cells exhibit osteoblast-like features and are capable of differentiating into cells of either cementogenic or osteogenic lineage. These cells are crucial for the maintenance of the integrity and regeneration of the periodontium (Somerman et al. (1990) Arch Oral Biol. 35: 241-47; Pitaru et al. (1994) J Periodontal Res. 29:81-94). Chronic infections in the periodontium, initiated by bacterial colonization, induce synthesis of pro-inflammatory cytokines, which can potentially affect PDL cell phenotype and function. These cytokines not only activate and recruit immune cells to the site of infection (Le and Vilcek (1987) J. Immunol. 139: 3330; Kunkel et al (1994) Ann. N.Y. Acad. Sci. 730:134), but also induce loss of supporting bone and ligamentous attachment (Pitaru et al. (1994) J Periodontal Res. 29:81-94). TNFα, for example, has been shown to modulate the PDL cell osteoblast-like phenotype and functions (Agarwal et al. (1998) Infect. Immun. 66:932-937). Additionally, TNFα and IL-1β change the phenotypic characteristics of osteoblasts by down-regulation of alkaline phosphatase (Kuroki et al. (1994) Rheumatology 33:224) and by the modulation of collagen, collagenase, proteoglycan, and prostaglandin syntheses (Agarwal et al. (1998) Infect. Immun. 66:932-937).

In the isolated PDL cells, IL-1β induces phenotypic changes (Agarwal et al. (1998) Infect. Immun. 66:932-937). PDL cells from healthy periodontium do not recognize bacterial lipopolysaccharide (LPS) nor do they elicit pro-inflammatory cytokines in response to LPS. Following IL-1β treatment, PDL cells lose their osteoblast-like characteristics while assuming a new LPS-responsive phenotype. Thus, IL-1β is an important regulator of PDL cell function and directs these cells to participate actively in an immune response during infections. IL-1β stimulates bone resorption and inhibits bone formation (Stashenko et al. (1987) J Bone Miner Res. 2:559-65; Nguyen et al. (1991) Lymphokine Cytokine Res. 10:15-21; Tatakis (1993) J Periodontol (1991) 64:416-31). In addition, IL-1β synergizes the bone-resorptive actions of TNF-α (Bertolini et al. (1986) Nature 319:516-18; van der Pluijm et al. (1991) Endocrinology 129:1596). Another important activity of IL-1β in the pathological process of periodontitis is to induce the production of matrix metalloproteinases (MMPs) (Havemose-Poulsen and Holmstrup (1997) Crit. Rev. Oral. Biol. Med 8:217). IL-1β gives rise to an elevated level of procollagenase in both gingival fibroblasts and PDL cells (Meikle et al. (1989) J Periodontal Res. 24:207-13; Lark et al. (1990) Connect Tissue Res. 25:49-65; Tewari et al. (1994) Arch Oral Biol. 39 657-64). In addition, IL-1β stimulates plasminogen activator in gingival fibroblasts, resulting in the generation of plasmin, which is an activator of several matrix metalloproteinases (Mochan et al. (1988) J Periodontal Res. 23:28-32). Furthermore, Stashenko and co-workers reported a positive correlation between IL-1β levels in gingival tissues and recent attachment loss (Stashenko et al. (1991) J Clin Periodontol 18:548-54).

TNFα is another key mediator of immune and inflammatory responses and has been found in measurable quantities in the areas of active periodontal inflammation (Rossomando et al. (1990) Arch Oral Biol. 35:431-34; Stashenko et al. (1991) J Clin Periodontol 18:548-54). TNFα changes the osteoblastic features of PDL cells (Quintero et al. (1995) J. Dent. Res. 74:1802). This is substantiated by their ability to express other pro-inflammatory cytokines, such as IL-1β, IL-6, and IL-8, in response to LPS. TNFα induces the secretion of collagenase by fibroblasts, resorption of cartilage and bone, and has been implicated in the destruction of periodontal tissue in periodontitis (Elias et al. (1987) J. Immunol. 138: 3812; Meikle et al. (1989) J Periodontal Res. 24:207-13; Chaudhary et al. (1992) Endocrinology 130:2528). In resting macrophages, TNFα induces the synthesis of IL-1β and prostaglandin E2. TNF-α also activates osteoclasts and thus induces bone resorption. TNF-α has synergistic effects with the bone-resorptive actions of IL-1β ((van der Pluijm et al. (1991) Endocrinology 129:1596; Bertolini et al. (1986) Nature 319:516-8; Johnson et al. (1989) Endocrinology 124: 1424).

In inflammatory periodontal lesions, a variety of cell types-such as T-cells, macrophages, endothelial cells, and fibroblasts-were shown to have increased IL-6 expression at both the mRNA and protein levels (Kono et al. (1991) J. Immunol. 146:1812; Matsuki et al (1992) Immunology 76:42-47; Fujihashi et al. (1993) Am. J. Pathol. 142:1239; Yarnazaki et al. (1994) J Oral Pathol Med. 23:347-53). Since IL-6 is of particular importance in human B cell responses, it has been speculated that the expansion of B-cells/plasma cells seen in periodontitis lesions may result from an increased production of IL-6 at diseased sites (Fujihashi et al (1993) J Periodontol 64:400-406). Additionally, IL-6 plays an important role in the local regulation of bone turnover (Lowik et al. (1989) Biochem Biophys Res Commun. 162:1546-52; Ishimi et al. (1990) J. Immunol. 145:3297; Kurihara et al. (1990) J. Immunol. 144:4226) and appears to be essential for bone loss caused by estrogen deficiency (Horowitz (1993) J Bone Miner Res. 8:1163-71). In vitro studies also demonstrated that simultaneous treatment of mouse osteoblastic cells and bone marrow cells with IL-6 and soluble IL-6 receptor strikingly induced osteoclast formation (Tamura et al. (1993) PNAS 90:11924). Furthermore, it was also suggested that IL-6 may act as an autocrine and/or paracrine factor in bone resorption in pathologic states by stimulating the formation of osteoclasts and the activation of osteoclastic bone resorption (Ohsaki et al. (1992) Endocrinology 131: 2229). These findings imply the involvement of IL-6 in the pathogenesis of periodontal tissue destruction in periodontitis.

Inhibition of the COX enzyme is the mechanism of action attributed to most non-steroidal anti-inflammatory drugs (NSAIDS). There are two distinct isoforms of the COX enzyme (COX-1 and COX-2), which share approximately 60% sequence homology, but differ in expression profiles and function. COX-1 is a constitutive form of the enzyme that has been linked to the production of physiologically important prostaglandins, which help regulate normal physiological functions, such as platelet aggregation, protection of cell function in the stomach and maintenance of normal kidney function. (Dannhardt and Kiefer (2001) Eur. J. Med. Chem. 36:109-26). The second isoform, COX-2, is a form of the enzyme that is inducible by pro-inflammatory cytokines, such as interleukin-1β (IL-1β) and other growth factors. (Herschmann (1994) Cancer Metastasis Rev. 134:241-56; Xie et al. (1992) Drugs Dev. Res. 25:249-65). This isoform catalyzes the production of prostaglandin $E_2$ (PGE2) from arachidonic acid (AA). Inhibition of COX is responsible for the anti-inflammatory activity of conventional NSAIDs.

Inhibitors that demonstrate dual specificity for COX and LOX would have the obvious benefit of inhibiting multiple pathways of arachidonic acid metabolism. Such inhibitors would block the inflammatory effects of prostaglandins (PG), as well as, those of multiple leukotrienes (LT) by limiting their production. This includes the vasodilation, vasopermeability and chemotactic effects of PGE2, LTB4, LTD4 and LTE4, also known as the slow reacting substance of anaphalaxis. Of these, LTB4 has the most potent chemotactic and chemokinetic effects. (Moore (1985) in *Prostanoids: pharmacololical physiological and clinical relevance*, Cambridge University Press, N.Y., pp. 229-230).

Because the mechanism of action of COX inhibitors overlaps that of most conventional NSAID's, COX inhibitors are used to treat many of the same symptoms, including pain and swelling associated with inflammation in transient conditions and chronic diseases in which inflammation plays a critical role. However, most of the known NSAIDs are not suitable for periodontal diseases due to their poor solubility and bioavailability.

Current methods for treating periodontal disease are limited with control of the infection being the primary goal (Genco et al. (1990) in *Contenporary Periodontics*, The C.V. Mosby Company, St. Louis, pp. 361-370). Common antimicrobial or anti-plaque agents include chlorhexidine, Triclosan, stannous fluoride, Listerine, hydrogen peroxide, cetylpyridimiun chloride and sanguinarine alkaloids. Prescription anti-microbial mouth rinse, antiseptic chip, antibiotic gel/micro-spheres and enzyme suppressant-doxycycline are the preferred non-mechanical/physical options to treat and control periodontal disease. Applicant is unaware of any reports of a formulation combining Free-B-Ring-Flavonoids and flavans as the primary biologically active components targeting the eicosanoid and cytokine pathways for the treatment of oral diseases and conditions.

Flavonoids or bioflavonoids are a widely distributed group of natural products, which have been reported to have antibacterial, anti-inflammatory, antiallergic, antimutagenic, antiviral, antineoplastic, anti-thrombic and vasodilatory activity. The structural unit common to this group of compounds includes two benzene rings on either side of a 3-carbon ring as illustrated by the following general structural formula:

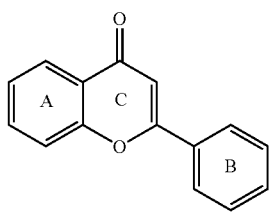

Various combinations of hydroxyl groups, sugars, oxygen and methyl groups attached to this general three ring structure create the various classes of flavonoids, which include flavanols, flavones, flavan-3-ols (catechins), anthocyanins and isoflavones.

Free-B-Ring flavones and flavonols are a specific class of flavonoids, which have no substituent groups on the aromatic B ring (referred to herein as Free-B-Ring flavonoids), as illustrated by the following general structure:

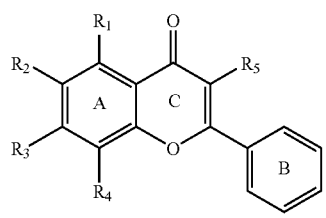

wherein
$R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a glycoside of a single or combination of multiple sugars, wherein said glycoside is linked to the 7-hydroxy chromone by a carbon, oxygen, nitrogen or sulfur, and wherein said single or combination of multiple sugars include, but are not limited to aldopentoses, methylaldopentose, aldohexoses, ketohexose and their chemical derivatives thereof;

wherein
R is an alkyl group having between 1-10 carbon atoms; and
X is selected from the group of pharmaceutically acceptable counter anions including, but not limited to hydroxyl, chloride, iodide, fluoride, sulfate, phosphate, acetate, carbonate, etc.

Free-B-Ring flavonoids are relatively rare. Out of 9,396 flavonoids synthesized or isolated from natural sources, only 231 Free-B-Ring flavonoids are known (*The Combined Chemical Dictionary*, Chapman & Hall/CRC, Version 5:1 June 2001). Free-B-Ring flavonoids have been reported to have diverse biological activity. Typically, flavonoids have been tested for biological activity randomly based upon their availability. Occasionally, the requirement of substitution on the B-ring has been emphasized for specific biological activity, such as the B-ring substitution required for high affinity binding to p-glycoprotein (Boumendjel et al. (2001) Bioorg. Med. Chem. Lett. 11(1):75-77); cardiotonic effect (Itoigawa et al. (1999) J. Ethnopharmacol. 65(3): 267-272), protective effect on endothelial cells against linoleic acid hydroperoxide-induced toxicity (Kaneko and Baba (1999) Biosci Biotechnol. Biochem 63(2):323-328), COX-1 inhibitory activity (Wang (2000) Phytomedicine 7:15-19) and prostaglandin endoperoxide synthase (Kalkbrenner et al (1992) Pharmacology 44(1):1-12). Few publications have mentioned the significance of the unsubstituted B ring of the Free-B-Ring flavonoids. One example is the use of 2-phenyl flavones, which inhibit NADPH quinone acceptor oxidoreductase, as potential anticoagulants. (Chen et al. (2001) Biochem. Pharmacol. 61(11):1417-1427).

The mechanism of action of the anti-inflammatory activity of various Free-B-Ring flavonoids has been controversial. The anti-inflammatory activity of the Free-B-Ring flavonoids, chrysin (Liang et al. (2001) FEBS Lett. 496(1):12-18), wogonin (Chi et al. (2001) Biochem. Pharmacol. 61:1195-1203) and halangin (Raso et al. (2001) Life Sci. 68(8):921-931), has been associated with the suppression of inducible cyclooxygenase and nitric oxide synthase via activation of peroxisome proliferator activated receptor gamma (PPARγ) and influence on degranulation and AA release. (Tordera et al. (1994) Z. Naturforsch [C] 49:235-240). It has been reported that oroxylin, baicalein and wogonin inhibit the activity of 12-lipoxygenase without affecting cyclooxygenase. (You et al. (1999) Arch. Pharm. Res. 22(1):18-24). More recently, the anti-inflammatory activity of wogonin, baicalin and baicalein has been reported as occurring via inhibition of inducible nitric oxide synthase and cox-2 gene expression induced by nitric oxide inhibitors and lipopolysaccharide. (Chen et al. (2001) Biochem. Pharmacol. 61(11):1417-1427). It has also been reported that oroxylin acts via suppression of NFκB activation. (Chen et al. (2001) Biochem. Pharmacol. 61(11):1417-1427). Finally, wogonin reportedly inhibits inducible PGE2 production in macrophages. (Wakabayashi and Yasui (2000) Eur. J. Pharmacol. 406 (3):477-481).

The Chinese medicinal plant, *Scuttellaria baicalensis* contains significant amounts of Free-B-Ring flavonoids, including baicalein, baicalin, wogonin and baicalenoside. Traditionally, this plant has been used to treat a number of conditions including clearing away heat, purging fire, dampness-warm and summer fever syndromes; polydipsia resulting from high fever; carbuncle, sores and other pyogenic skin infections; upper respiratory infections, such as acute tonsillitis, laryngopharyngitis and scarlet fever; viral hepatitis; nephritis; pelvitis; dysentery; hematemesis and epistaxis. This plant has also traditionally been used to prevent miscarriage. (*Encyclopedia of Chinese Traditional Medicine*, ShangHai Science and Technology Press, ShangHai, China, 1998). Clinically *Scutellaria* is now used to treat conditions such as pediatric pneumonia, pediatric bacterial diarrhea, viral hepatitis, acute gallbladder inflammation, hypertension, topical acute inflammation, resulting from cuts and surgery, bronchial asthma and upper respiratory infections. (*Encyclopedia of Chinese Traditional Medicine*, ShangHai Science and Technology Press, ShangHai, China, 1998). The pharmacological efficacy of *Scuttellaria* roots for treating bronchial asthma is reportedly related to the presence of Free-B-Ring flavonoids and their suppression of eotaxin associated recruitment of eosinophils. (Nakajima et al. (2001) Planta Med. 67(2):132-135).

To date, a number of naturally occurring Free-B-Ring flavonoids have been commercialized for varying uses. For example, liposome formulations of *Scutellaria* extracts have been utilized for skin care (U.S. Pat. Nos. 5,643,598; 5,443, 983). Baicalin has been used for preventing cancer, due to its inhibitory effects on oncogenes (U.S. Pat. No. 6,290,995). Baicalin and other compounds have been used as antiviral, antibacterial and immunomodulating agents (U.S. Pat. No. 6,083,921 and WO98/42363) and as natural anti-oxidants (WO98/49256 and Poland Pub. No. 9,849,256). Flavonoids formulates with terpenoids have been used as inhibitors of surface-bound glusosyltransferase for treating and inhibiting dental caries (US#20040057908). Japanese Pat. No. 63027435 describes the extraction, and enrichment of baicalein and Japanese Pat. No. 61050921 describes the purification of baicalin.

U.S. application Ser. No. 10/091,362, filed Mar. 1, 2002, entitled "Identification of Free-B-Ring Flavonoids as Potent COX-2 Inhibitors," and U.S. application Ser. No. 10/427,746, filed Jul. 22, 2003, entitled "Formulation of a Mixture of Free-B-Ring Flavonoids and Flavans as a Therapeutic Agent" disclose a method for inhibiting the cyclooxygenase enzyme COX-2 by administering a composition comprising a Free-B-Ring flavonoid or a composition containing a mixture of Free-B-Ring flavonoids to a host in need thereof. This is the first report of a link between Free-B-Ring flavonoids and COX-2 inhibitory activity. These applications are specifically incorporated herein by reference in their entirety.

Flavans include compounds illustrated by the following general structure:

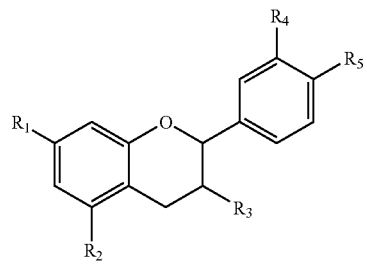

wherein
$R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters, and their chemical derivatives thereof, a glycoside of a single or combination of multiple sugars, wherein said glycoside is linked to the 7-hydroxy chromone by a carbon, oxygen, nitrogen or sulfur, and wherein said single or combination of multiple sugars include, but are not limited to aldopentoses, methylaldopentose, aldohexoses, ketohexose and their chemical derivatives thereof and other polymerized flavans;
wherein
R is an alkyl group having between 1-10 carbon atoms; and
X is selected from the group of pharmaceutically acceptable counter anions including, but not limited to hydroxyl, chloride, iodide, sulfate, phosphate, acetate, fluoride, and carbonate, etc.

Catechin is a flavan, found primarily in green tea, having the following structure:

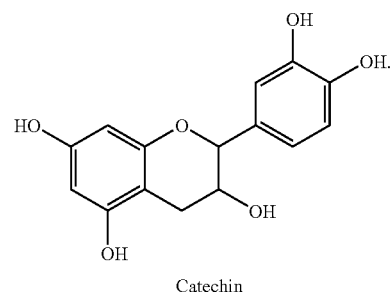 [SMILES: Oc1cc(O)c2c(c1)OC(c1ccc(O)c(O)c1)C(O)C2]

Catechin

Catechin works both alone and in conjunction with other flavonoids found in tea, and has both antiviral and antioxidant activity. Catechin has been shown to be effective in the treatment of viral hepatitis. It also appears to prevent oxidative damage to the heart, kidney, lungs and spleen and has been shown to inhibit the growth of stomach cancer cells.

Catechin and its isomer epicatechin inhibit prostaglandin endoperoxide synthase with an IC$_{50}$ value of 40 μM. (Kalkbrenner et al. (1992) Pharmacol. 44:1-12). Commercially available pure (+)-catechin inhibits COX-1 with an IC$_{50}$ value of around 183 to 279 μM depending upon the experimental conditions, with no selectivity for COX-2. (Noreen et al. (1998) J. Nat. Prod. 61:1-7). Green tea catechin, when supplemented into the diets of Sprague Dawley male rats, lowered the activity level of platelet PLA$_2$ and significantly reduced platelet cyclooxygenase levels. (Yang et al. (1999) J. Nutr. Sci. Vitaminol. 45:337-346). Catechin and epicatechin reportedly weakly suppress cox-2 gene transcription in human colon cancer DLD-1 cells (IC$_{50}$=415.3 μM). (Mutoh et al. (2000) Jpn. J. Cancer Res. 91:686-691). The neuroprotective ability of (+)-catechin from red wine results from the antioxidant properties of catechin, rather than inhibitory effects on intracellular enzymes, such as cyclooxygenase, lipoxygenase, or nitric oxide synthase (Bastianetto et al. (2000) Br. J. Pharmacol. 131:711-720). Catechin derivatives purified from green and black tea, such as epigallocatechin-3-gallate (EGCG), epigallocatechin (EGC), epicatechin-3-gallate (ECG), and theaflavins showed inhibition of cyclooxygenase and lipoxygenase dependent metabolism of AA in human colon mucosa and colon tumor tissues (Hong et al. (2001) Biochem. Pharmacol. 62:1175-1183) and induce cox-2 expression and PGE$_2$ production (Park et al. (2001) Biochem. Biophys. Res. Commun. 286:721-725).

*Acacia* is a genus of leguminous trees and shrubs. The genus *Acacia* includes more than 1000 species belonging to the family of Leguminosae and the subfamily of Mimosoideae. *Acacias* are distributed worldwide in tropical and subtropical areas of Central and South America, Africa, parts of Asia, as well as, Australia, which has the largest number of endemic species. To date, approximately 330 compounds have been isolated from various *Acacia* species. Flavonoids are the major class of compounds isolated from *Acacias*. Approximately 180 different flavonoids have been identified, 111 of which are flavans. Terpenoids are second largest class of compounds isolated from species of the *Acacia* genus, with 48 compounds having been identified. Other classes of compounds isolated from *Acacia* include, alkaloids (28), amino acids/peptides (20), tannins (16), carbohydrates (15), oxygen heterocycles (15) and aliphatic compounds (10). (Buckingham, *The Combined Chemical Dictionary*, Chapman & Hall CRC, version 5:2, December 2001).

Phenolic compounds, particularly flavans are found in moderate to high concentrations in all *Acacia* species. (Abdulrazak et al. (2000) Journal of Animal Sciences. 13:935-940). Historically, most of the plants and extracts of the *Acacia* genus have been utilized as astringents to treat gastrointestinal disorders, diarrhea, indigestion and to stop bleeding. (Vautrin (1996) Universite Bourgogne (France) European abstract 58-01C:177; Saleem et al. (1998) Hamdard Midicus. 41:63-67). The extract from the bark of *Acacia* has been patented in Japan for external use as a whitening agent (Abe, JP 10025238), as a glucosyl transferase inhibitor for dental applications (Abe, JP 07242555), as a protein synthesis inhibitor (Fukai, JP 07165598), as an active oxygen scavenger for external skin preparations (Honda, JP 07017847, Bindra U.S. Pat. No. 6,126,950), and as an inhibitor of hyaluronidase to prevent inflammation, pollinosis and cough (Ogura, JP 07010768).

The *Uncaria* genus, includes 34 species many of which are well known as medicinal plants. *Uncaria* plants have been utilized by different cultures for treatment of wounds, and ulcers, fevers, headaches, gastrointestinal illnesses and microbial/gungal infections. *Uncaria* plants contain significant amounts of catechin and other flavones. Other components that have been reported in *Uncaria* genus include alkaloids, terpenes, quinovic acid glycosides, coumarins, and flavonoids. *Uncaria gambir* is a species common in Malaysia, Singapore, India and other South East Asian countries. Catechins are major components in the whole plant of *Uncaria gambir*.

SUMMARY OF THE INVENTION

The present invention includes methods that are effective in simultaneously inhibiting both the eicosanoid system and the cytokine system for use in the prevention and treatment of diseases and conditions related to the mouth, teeth and gums. The method for the simultaneous dual modulation of both the eicosanoid system and the cytokine system is comprised of administering, systemically or locally, a composition comprised of a mixture of Free-B-Ring flavonoids and flavans synthesized and/or isolated from a single plant or multiple plants to a host in need thereof. This composition of matter is referred to herein as UP676. The efficacy and safety of this method is demonstrated with purified enzymes, in different cell lines, in multiple animal models and eventually in a human clinical study. The ratio of the Free-B-Ring flavonoids to flavans in the composition is in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* or *Uncaria* genus of plants.

The present invention also includes methods for the prevention and treatment of diseases and conditions of the mouth, teeth and gums. The method for preventing and treating said diseases and conditions of the mouth, teeth and gums is comprised of administering, systemically or topically, to a host in need thereof an effective amount of a composition comprising a mixture of Free-B-Ring flavonoids and flavans synthesized and/or isolated from a single plant or multiple plants and a pharmaceutically acceptable carrier. The ratio of the Free-B-Ring flavonoids to flavans in the composition is in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* or *Uncaria* genus of plants.

The Free-B-Ring flavonoids, also referred to herein as Free-B-Ring flavones and flavonols, that can be used in accordance with the following invention include compounds illustrated by the following general structure:

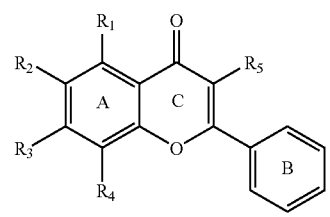

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a glycoside of a single or combination of multiple sugars, wherein said glycoside is linked to the 7-hydroxy chromone by a carbon, oxygen, nitrogen or sulfur, and wherein said single or combination of multiple sugars include, but are not limited to aldopentoses, methylaldopentose, aldohexoses, ketohexose and their chemical derivatives thereof;

wherein

R is selected from an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The Free-B-Ring flavonoids of this invention may be obtained by synthetic methods or extracted from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*.

The flavans that can be used in accordance with the following invention include compounds illustrated by the following general structure:

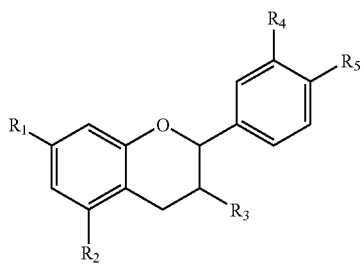

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters, and their chemical derivatives thereof; a glycoside of a single or combination of multiple sugars, wherein said glycoside is linked to the 7-hydroxy chromone by a carbon, oxygen, nitrogen or sulfur, and wherein said single or combination of multiple sugars include, but are not limited to aldopentoses, methylaldopentose, aldohexoses, ketohexose and their chemical derivatives thereof and other polymerized flavans;

wherein

R is selected from an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The flavans of this invention may be obtained from a plant or plants selected from the genus of *Acacia* or *Uncaria*. In a preferred embodiment, the plant is selected from the group consisting of *Acacia catechu, Acacia concinna, Acacia farnesiana, Acacia Senegal, Acacia speciosa, Acacia arabica, A. caesia, A. pennata, A. sinuata. A. mearnsii, A. picnantha, A. dealbata, A. auriculiformis, A. holoserecia* and *A. mangium*; and *Uncaria gambir, Uncaria lanosa, Uncaria hirsute, Uncaria africana, Uncaria elliptica, Uncaria orientalis, Uncaria attenuate, Uncaria acida, Uncaria homomalla, Uncaria sessilifructus, Uncaria sterrophylla, Uncaria bernaysii, Uncaria sinensis, Uncaria callophylla, Uncaria rhychophylla, Uncaria tomentosa, Uncaria longiflora, Uncaria hirsute, Uncaria cordata,* and *Uncaria borneensis*.

In one embodiment, the present invention includes a method for preventing and treating a number of diseases and conditions related to the mouth, gums and teeth including, but not limited to periodontal (gum) diseases such as gingivitis, aggressive periodontitis, chronic periodontitis, periapical periodontitis, periodontitis as a manifestation of systemic diseases, and necrotizing periodontal disease, wherein the causes of said periodontal diseases include, but are not limited to chronic bacterial infection, plaque accumulation, tobacco usage by smoking and/or chewing, genetically susceptibility, caused by pregnancy and puberty, stress, medications, and diabetes, poor nutrition and other systemic diseases.

In another embodiment, the present invention includes a method for the prevention and treatment of sensitive gums and teeth, sequelae, pulpitis, irritation, pain and inflammation caused by the physical implantation of oral dentures, trauma, injuries, bruxism and other minor wounds in mouth, on the gums or on the tongue, dental plague and calculus, tooth decalcification, proteolysis and caries (decay).

The present invention further includes therapeutic compositions comprising the therapeutic agents of the present invention. In addition to their use for the prevention and treatment of the above described diseases and conditions of the mouth, teeth and gums, the therapeutic compositions described herein can also be useful for maintaining optimum saliva production, saliva pH value, minimizing bacterial growth, reducing the formation of plague acids, inhibiting mineral loss, promoting remineralization, reducing the prevalence of caries, yielding a healthy gums, whitening teeth, maintaining healthy oral hygiene and reducing oral malodour (halitosis).

The method of prevention and treatment according to this invention comprises administering systemically or topically to a host in need thereof a therapeutically effective amount of the formulated Free-B-Ring flavonoids and flavans isolated from a single source or multiple sources. The purity of the individual and/or a mixture of multiple Free-B-Ring flavonoids and flavans includes, but is not limited to 0.01% to 100%, depending on the methodology used to obtain the compound(s). In a preferred embodiment, doses of the mixture of Free-B-Ring flavonoids and flavans containing the same are an efficacious, nontoxic quantity generally selected from the range of 0.001% to 100% based on total weight of the topical formulation. Persons skilled in the art using routine clinical testing are able to determine optimum doses for the particular ailment being treated.

The present invention includes an evaluation of different compositions of Free-B-Ring flavonoids and flavans using enzymatic and in vivo models to optimize the formulation and obtain the desired physiological activity. The efficacy and safety of this formulation is demonstrated in human clinical studies. The compositions of this invention can be administered by any method known to one of ordinary skill in the art. The modes of administration include, but are not limited to, enteral (oral) administration, parenteral (intravenous, subcutaneous, and intramuscular) administration and topical application. In the one embodiment the method of treatment according to this invention comprises administering topically to a host in need thereof a therapeutically effective amount of a mixture of Free-B-Ring flavonoids and flavans synthesized and/or isolated from a single plant or multiple plants. Methods for topical administration include, but are not limited to a toothpaste, gel, ointment, mouthwash, chewing gum, tinctures, drinks and as well as other known pharmaceutical formulations.

To date, the applicants of the current invention are unaware of any reports of a formulation combining Free-B-Ring-Flavonoids and flavans as the primary biologically active components for the treatment of diseases and conditions related to the mouth, teeth and gums. The lack of substitution of one of the aromatic rings of the Free-B-Ring flavonoid plays very important role in making these compounds efficacious for use in oral care. Unlike many other anti-inflammatory drugs and natural occurring compounds, Free-B-Ring flavonoids, such as baicalin, has a low polarity aromatic ring on one side of the molecule and high polarity glucuronide and two hydroxyl groups on the other side. This structural arrangement allows these compounds to easily penetrate and remain in gum tissue. The combination of Free-B-Ring-flavonoids with flavans to produce the composition of matter referred to herein as UP676, offers a synergistic and potent modulator of both the eicosanoid system and the cytokine system that will help to control inflammation of the periodontal tissues, including inflammation in all four stages of periodontal disease. Additionally, due to the different biological availability, i.e. rate and percentage of biologically active compounds penetrating the epithelial cell membrane and the local concentrations of biologically active compounds in periodontal tissues, the combination of the two different type of compounds (higher polarity flavans vs. lower polarity Free-B-Ring flavonoids) offers both quick, on-site pain and acute-inflammatory relief by the biologically active flavans, as well as, longer lasting modulation of chronic inflammation in periodontal tissues by the biologically active Free-B-Ring flavonoids. Finally, in the preferred embodiment formulation of significant amounts of free-B-Ring flavonoids (80% by weight) with comparatively lower concentration of flavans (20% by weight), the more potent anti-oxidative flavans will function both as natural preservatives against oxidative degradation of the Free-B-Ring flavonoids and to neutralize and buffer the composition allowing delivery of the major active components—the Free-B-Ring flavonoids at the optimum pH and ionization conditions.

It is to be understood that both the foregoing general description and the following detailed description are exemplary and explanatory only and are not restrictive of the invention as claimed.

BRIEF DESCRIPTION OF THE DRAWINGS

With reference to FIG. 14, it can be seen that topical applications of UP676, both before and after UV radiation, significantly reduced erythema scores as compared with the control group and the group that was administered the standard treatment agent-Sooth-a-caine.

DETAILED DESCRIPTION OF THE PREFERRED EMBODIMENT

Figure 1:
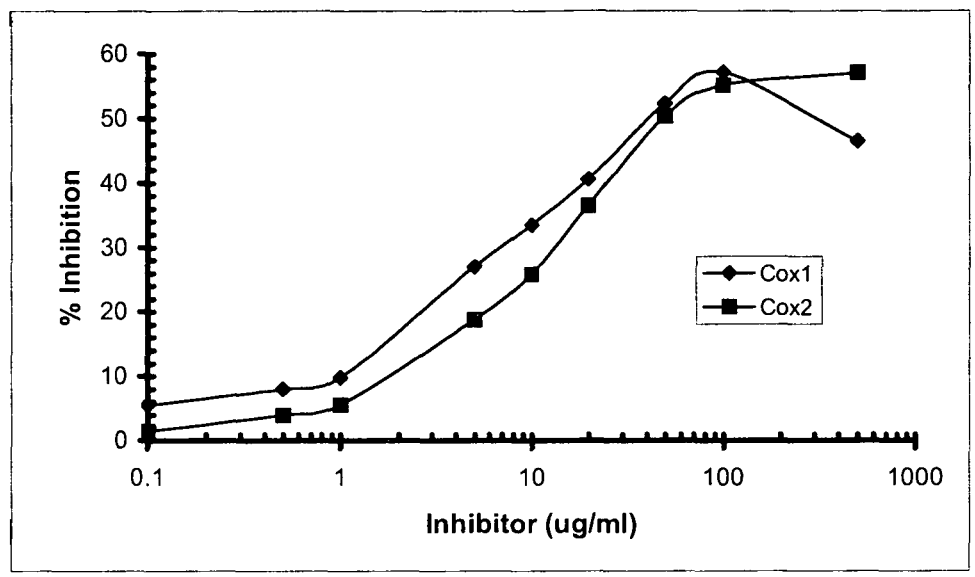
FIG. 1 depicts graphically a profile of the inhibition of COX-1 and COX-2 by a standardized Free-B-Ring flavonoid extract (83% baicalin based on HPLC), which was isolated from S. baicalensis. The extract was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was calculated as 0.24 μg/mL/unit of enzyme while the $IC_{50}$ for COX-2 was calculated as 0.48 μg/mL/unit.

Various terms are used herein to refer to aspects of the present invention. To aid in the clarification of the description of the components of this invention, the following definitions are provided.

It is to be noted that the term "a" or "an" entity refers to one or more of that entity; for example, a flavonoid refers to one or more flavonoids. As such, the terms "a" or "an", "one or more" and "at least one" are used interchangeably herein.

"Free-B-Ring Flavonoids" as used herein are a specific class of flavonoids, which have no substitute groups on the aromatic B-ring, as illustrated by the following general structure:

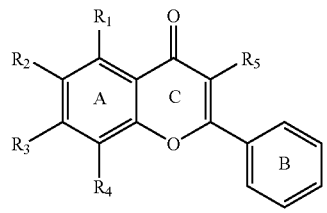

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a glycoside of a single or combination of multiple sugars wherein said glycoside is linked to the 7-hydroxy chromone by a carbon, oxygen, nitrogen or sulfur, and wherein said single or combination of multiple sugars include, but are not limited to aldopentoses, methylaldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Flavans" as used herein refer to a specific class of flavonoids, which can be generally represented by the following general structure:

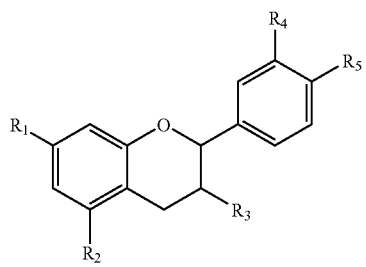

wherein $R_1$, $R_2$, $R_3$, $R_4$ and $R_5$ are independently selected from the group consisting of H, —OH, —SH, —OCH$_3$, —SCH$_3$, —OR, —SR, —NH$_2$, —NRH, —NR$_2$, —NR$_3^+$X$^-$, esters of the mentioned substitution groups, including, but not limited to, gallate, acetate, cinnamoyl and hydroxyl-cinnamoyl esters, trihydroxybenzoyl esters and caffeoyl esters, and their chemical derivatives thereof; a glycoside of a single or combination of multiple sugars, wherein said glycoside is linked to the 7-hydroxy chromone by a carbon, oxygen, nitrogen or sulfur, and wherein said single or combination of multiple sugars include, but are not limited to aldopentoses, methylaldopentose, aldohexoses, ketohexose and their chemical derivatives thereof and other polymerized flavans;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Therapeutic" as used herein, includes treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

"Placebo" refers to the substitution of the pharmaceutically or therapeutically effective dose or amount dose sufficient to induce a desired biological that may alleviate the signs, symptoms or causes of a disease with a non-active substance.

A "host" or "patient" is a living subject, human or animal, into which the compositions described herein are administered. Thus, the invention described herein may be used for veterinary as well as human applications and the terms "patient" or "host" should not be construed in a limiting manner. In the case of veterinary applications, the dosage ranges can be determined as described below, taking into account the body weight of the animal.

As used herein a "pharmaceutically acceptable carrier" refers to any carrier, which does not interfere with effectiveness of the biological activity of the active ingredient and which is not toxic to the host to which it is administered. Examples of "pharmaceutically acceptable carriers" include, but are not limited to, any of the standard pharmaceutical carriers such as a saline solution, i.e. Ringer's solution, a buffered saline solution, water, a dextrose solution, serum albumin and other excipients and preservatives for tableting and capsulating formulations.

"Gene expression" refers to the transcription of a gene to mRNA.

"Protein expression" refers to the translation of mRNA to a protein.

"RT-qPCR" as used herein refers to a method for reverse transcribing (RT) an mRNA molecule into a cDNA molecule and then quantitatively evaluating the level of gene expression using a polymerase chain reaction (PCR) coupled with a fluorescent reporter.

Note that throughout this application various citations are provided. Each citation is specifically incorporated herein in its entirety by reference.

The current invention provides methods for the extraction (Example 1, Table 1) of plants that contain Free-B-Ring flavonoids, including three species from the *Scutellaria* genus and *Oroxulum indicum* and plants that contain flavans, including *Acacia catechu* and three species from the *Uncaria* genus with organic and aqueous solvents. The crude extracts were assayed for cyclooxygenase inhibitory activity (Example 2, Tables 2 and 3). Purified Free-B-Ring flavonoids and flavans demonstrated inhibitory activity against cyclooxygenase (COX) and lipoxygenase (LOX), respectively, as shown in Examples 3 and 4 and Table 4. Methods for analyzing and quantifying the extracts are described in Examples 5 and 6 and the procedures to generate standardized Free-B-Ring flavonoids and flavans from botanical origins are provided in Examples 7 and 8.

In one embodiment of the present invention, the standardized Free-B-Ring flavonoid extract is comprised of the active compounds having a purity of between 1-99% (by weight) of total Free-B-Ring flavonoids as defined in Examples 1, 2, 5 and 8. Baicalin is the major active component in the extract derived from *Scutellaria* species, which accounts for approximately 50-90% (by weight) of the total Free-B-Ring flavonoids. In a preferred embodiment (Example 9), the standardized extract derived from *Scutellaria* species contains >82% total Free-B-Ring flavonoids in which the major component by weight of Free-B-Ring flavonoids is baicalin (see Table 11).

In one embodiment, the standardized flavan extract is comprised of the active compounds having a purity of between 1-99% (by weight) total flavans as defined in Examples 1, 4, 6 and 7. Catechin is the major active component in the extracts derived from both *Acacia catechu* and *Uncaria gambir* that accounts for 30-95% (by weight) of the total flavans. In a preferred embodiment (Example 9), the standardized flavan extract derived from *Acacia catechu* contains >80% of catechins.

In one embodiment, UP676 is produced by mixing the above two extracts or synthetic compounds in a ratio from 99:1 to 1:99. The preferred weight by weight ratios of Free-B-Ring flavonoids to flavans are 80:20 as defined in Example 9 and Table 11.

The concentration of Free-B-Ring flavonoids in UP676 can be from about 1% to 99% and the concentration of flavans in UP676 can be from 99% to 1%. In a preferred embodiment of the invention as set forth in Example 9 and Table 11, the concentration of total Free-B-Ring flavonoids in UP676 is approximately 75% with a baicalin content of approximately 60% of total weight of the UP676; and the concentration of total flavans in UP676 is approximately 10% with a catechin content of approximately 9.9%. In this embodiment, the total active components (Free-B-Ring flavonoids plus flavans) in UP676 are >85% of the total weight.

The present invention includes methods that are effective in simultaneously inhibiting both the eicosanoid and cytokine pathways, for use in the prevention and treatment of periodontal diseases and gingival conditions. The method for the dual modulation of the eicosanoid and cytokine pathways is comprised of administering, systemically or topically a composition comprised of a mixture of Free-B-Ring flavonoids and flavans synthesized and/or isolated from a single plant or multiple plants to a host in need thereof. This composition of matter is referred to herein as UP676. The efficacy of this method is demonstrated with purified enzymes, in different cell lines, in multiple animal models and eventually in a human clinical study. The ratio of the Free-B-Ring flavonoids to flavans in the composition is in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* genus of plants.

The present invention also includes methods that simultaneously inhibit cycloxygenase (COX) and lipoxygenase (LOX) enzymatic activity. The method for simultaneously inhibiting cycloxygenase (COX) and lipoxygenase (LOX) enzymatic activity is comprised of administering, systemically or topically, to a host in need thereof an effective amount of a composition comprised of a mixture of Free-B-Ring flavonoids and flavans synthesized and/or isolated from a single plant or multiple plants and a pharmaceutically acceptable carrier. The ratio of the Free-B-Ring flavonoids to flavans in the composition can be in the range of 99.9:0.1 of Free-B-Ring flavonoids:flavans to 0.1:99.9 Free-B-Ring flavonoids: flavans. In specific embodiments of the present invention, the ratio of Free-B-ring flavonoids to flavans is selected from the group consisting of approximately 90:10, 80:20, 70:30, 60:40, 50:50, 40:60, 30:70, 20:80 and 10:90. In a preferred embodiment of this invention, the ratio of Free-B-Ring flavonoids:flavans in the composition of matter is 80:20. In a preferred embodiment, the Free-B-Ring flavonoids are isolated from a plant or plants in the *Scutellaria* genus of plants and the flavans are isolated from a plant or plants in the *Acacia* genus of plants.

Also included in the present invention is a method for the simultaneous reduction of IL-1β, TNFα and IL-6, as well as, other proteins related to inflammation for use in the prevention and treatment of diseases and conditions related to the mouth, gums and teeth. While not limited by theory it is believed that the mechanism for reducing these proteins is the result of the down regulation of their gene expression by the composition of matter of the instant invention. The pro-inflammatory cytokines, especially IL-1β, TNFα and IL-6, play key roles in the chronic infections in the periodontium. Induction of the synthesis of the pro-inflammatory cytokines affects PDL cell phenotype and function. These cytokines not only activate and recruit immune cells to the site of infection, but also induce loss of supporting bone and ligamentous attachment. The method for the simultaneous suppression of the pro-inflammatory cytokine gene expression, especially of IL-1β, TNFα and IL-6, is comprised of administering, systemically or topically to a host in need thereof a composition comprised of a mixture of Free-B-Ring flavonoids and flavans synthesized and/or isolated from a single plant or multiple plants to a host in need thereof. This composition of matter is referred to herein as UP676. The ratio of the Free-B-Ring flavonoids to flavans in the composition is in the range of 99.9:0.1 of Free-B-Ring flavonoids:flavans to 0.1:99.9 Free-B-Ring flavonoids:flavans. In specific embodiments of the present invention, the ratio of Free-B-Ring flavonoids to flavans is selected from the group consisting of approximately 90:10, 80:20, 70:30, 60:40, 50:50, 40:60, 30:70, 20:80 and 10:90. In one preferred embodiment of this invention, the ratio of Free-B-Ring flavonoids:flavans in the composition of matter is 20:80. In another preferred embodiment, the Free-B-Ring flavonoids are isolated from a plant or plants in the *Scutellaria* genus of plants and the flavans are isolated from a plant or plants in the *Acacia* genus of plants.

In one embodiment, the present invention includes a method for preventing and treating a number of diseases and conditions related to the mouth, gums and teeth including, but not limited to periodontal (gum) diseases including gingivitis, aggressive periodontitis, chronic periodontitis, periapical periodontitis, periodontitis as a manifestation of systemic diseases, and necrotizing periodontal disease, wherein the causes of said periodontal diseases include, but are not limited to chronic bacterial infection, plaque accumulation, tobacco usage by smoking and/or chewing, genetically susceptible, caused by pregnancy and puberty, stress, medications, and diabetes, poor nutrition and other systemic diseases.

In another embodiment, the present invention includes a method for the prevention and treatment of sensitive gums and teeth, sequelae, pulpitis, irritation and pain caused by physical implantation of oral dentures and other materials, a method for promoting wound healing, reducing pain and inflammation caused by trauma, injuries, bruxism and other minor wounds in mouth, on the gums or on the tongue. In yet another embodiment, the present invention includes a method for the prevention and treatment of dental plague and calculus, tooth decalcification, proteolysis and caries (decay).

The present invention further includes therapeutic compositions comprising the therapeutic agents of the present invention. In addition to their use for the prevention and treatment of the above described diseases and conditions of the mouth, teeth and gums, the therapeutic compositions described herein can also be useful for maintaining optimum saliva production, saliva pH value, minimizing bacterial growth, reducing the formation of plague acids, inhibiting mineral loss, promoting remineralization, reducing the prevalence of caries, yielding a healthy gums, whitening teeth, maintaining healthy oral hygiene and reducing oral malodour (halitosis).

The Free-B-Ring flavonoids that can be used in accordance with the instant invention include compounds illustrated by the general structure set forth above. The Free-B-Ring flavonoids of this invention may be obtained by synthetic methods or may be isolated from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae, and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus* and *Alpinia*. The flavonoids can be found in different parts of plants, including but not limited to stems, stem barks, twigs, tubers, roots, root barks, young shoots, seeds, rhizomes, flowers and other reproductive organs, leaves and other aerial parts.

Methods for the isolation and purification of Free-B-Ring flavonoids are described in U.S. application Ser. No. 10/091,362, filed Mar. 1, 2002, entitled "Identification of Free-B-Ring Flavonoids as Potent Cox-2 Inhibitors," and U.S. application Ser. No. 10/469,275, filed Aug. 27, 2003, entitled "Identification of Free-B-Ring Flavonoids as Potent Cox-2 Inhibitors," each of which is incorporated herein by reference in its entirety.

The flavans that can be used in accordance with the method of this invention include compounds illustrated by the general structure set forth above. The flavans of this invention are isolated from a plant or plants selected from the *Acacia* or *Uncaria* genus of plants. In a preferred embodiment, the plant is selected from the group consisting of *Acacia catechu* (*A. catechu*), *A. concinna, A. farnesiana, A. Senegal, A. speciosa, A. arabica, A. caesia, A. pennata, A. sinuata. A. mearnsii, A. picnantha, A. dealbata, A. auriculiformis, A. holoserecia* and *A. mangium*; or *Uncaria gambir, Uncaria lanosa, Uncaria hirsute, Uncaria africana, Uncaria elliptica, Uncaria orientalis, Uncaria attenuate, Uncaria acida, Uncaria homomalla, Uncaria sessilifructus, Uncaria sterrophylla, Uncaria bernaysii, Uncaria sinensis, Uncaria callophylla, Uncaria rhychophylla, Uncaria tomentosa, Uncaria longiflora, Uncaria hirsute, Uncaria cordata*, and *Uncaria borneensis*. The flavans can be found in different parts of plants, including but not limited to stems, stem barks, trunks, trunk barks, twigs, tubers, roots, root barks, young shoots, seeds, rhizomes, flowers and other reproductive organs, leaves and other aerial parts.

Methods for the isolation and purification of flavans are described in U.S. application Ser. No. 10/104,477, filed Mar. 22, 2002, entitled "Isolation of a Dual Cox-2 and 5-Lipoxygenase Inhibitor from *Acacia*," which is incorporated herein by reference in its entirety.

The present invention implements a strategy that combines a series of in vivo inflammation and toxicity studies as well as in vitro biochemical, cellular, and gene expression screens to identify active plant extracts that specifically inhibit COX and LOX enzymatic activity, impact mRNA gene expression and reduce inflammation. The methods used herein to identify active plant extracts that specifically inhibit COX and LOX are described in Examples 1 and 2, as well as in U.S. application Ser. No. 10/091,362, filed Mar. 1, 2002, entitled "Identification of Free-B-Ring Flavonoids as Potent Cox-2 Inhibitors;" U.S. application Ser. No. 10/104,477, filed Mar. 22, 2002, entitled "Isolation of a Dual Cox-2 and 5-Lipoxygenase Inhibitor from *Acacia*," and U.S. application Ser. No. 10/427, 746, filed Apr. 30, 2003, entitled "Formulation With Dual Cox-2 And 5-Lipoxygenase Inhibitory Activity," each of which is incorporated herein by reference in its entirety.

Various uses of the composition of this invention are described in U.S. application Ser. No. 10/785,704, filed Feb. 24, 2004, entitled "Inhibition of Carbohydrate Induced Obesity with a Defined Plant Extract," U.S. application Ser. No. 10/817,330, filed Apr. 2, 2004, entitled "Formulation of Dual COX-2 and 5-Lipoxygenase Inhibitors for Mammal Skin Care," U.S. application Ser. No. 10/932,571, filed Sep. 1, 2004, entitled "Formulation With Dual COX-2 and 5-Lipoxygenase Inhibitory Activity for Use in the Prevention and Treatment of Cognitive Decline and Age-Related Memory Impairments, and" U.S. application Ser. No. 60/605,110, filed Aug. 27, 2004, entitled "Therapeutic Agent for the Down-Regulation of Multiple Cytokine Genes." Each of these applications is incorporated herein by reference in its entirety.

Figure 6:
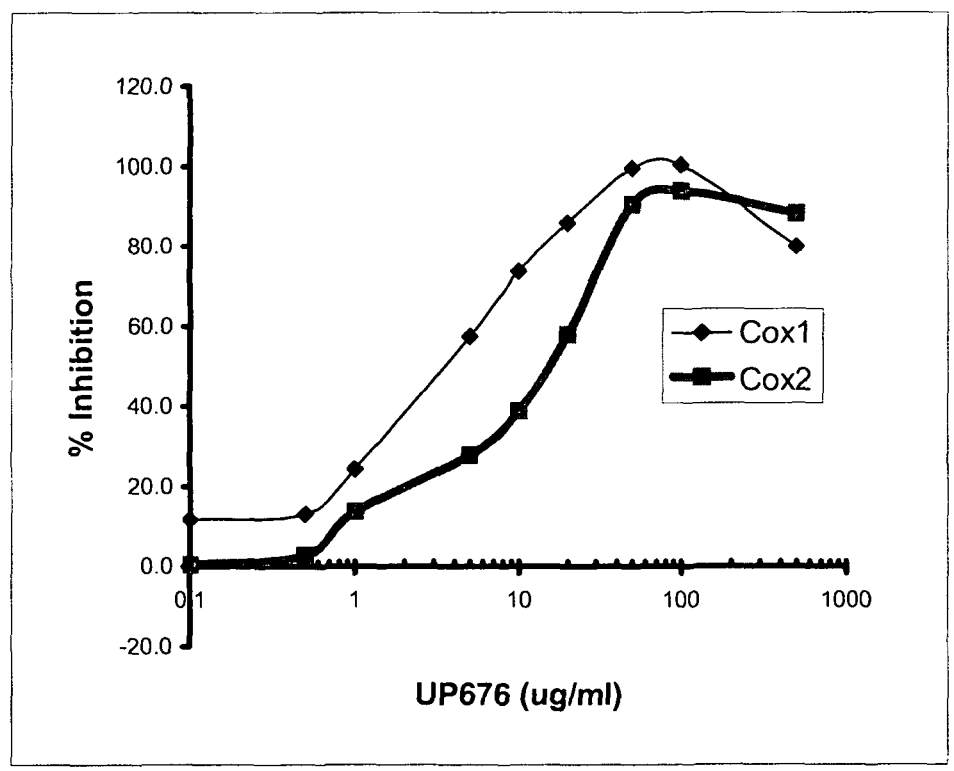
FIG. 6 depicts graphically a profile of the inhibition of COX-1 and COX-2 by a formulation produced by combining an extract of Free-B-Ring flavonoids isolated from the roots of S. baicaleinsis and an extract of flavans isolated from the bark of A. catechu in a ratio of 80:20. This composition of matter, referred to hereinafter as UP676, was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was 2 μg/mL/unit of enzyme while the $IC_{50}$ for COX-2 was 4 μg/mL/unit.
Figure 7:
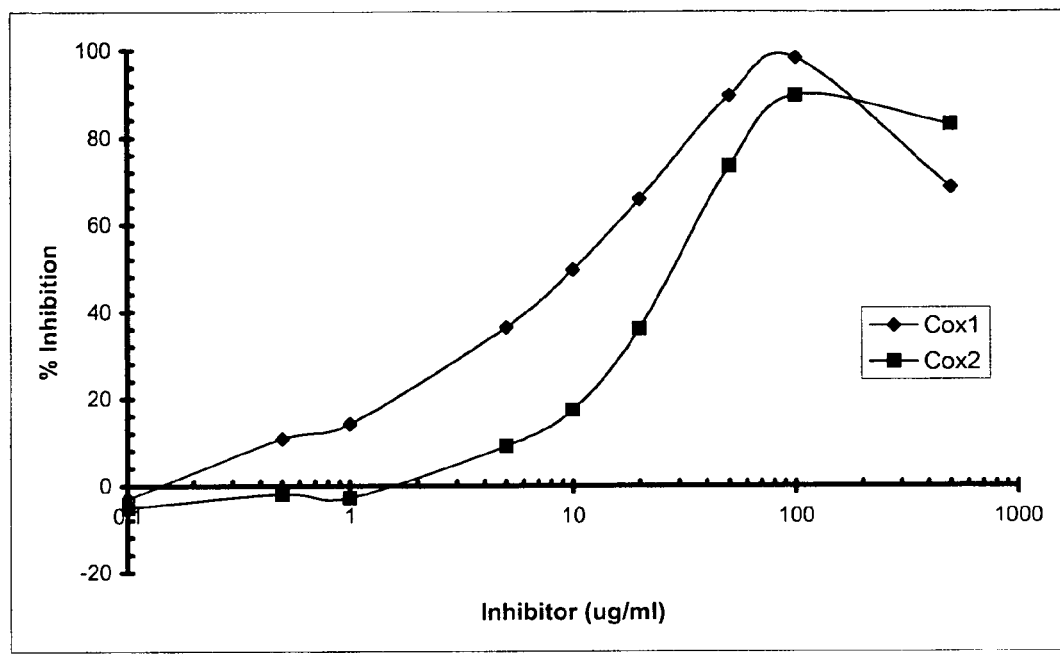
FIG. 7 depicts graphically a profile of the inhibition of COX-1 and COX-2 by a formulation produced by combining an extract of Free-B-Ring flavonoids isolated from the roots of S. baicalensis and an extract of flavans isolated from the bark of A. catechu in a ratio of about 50:50. The composition was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was calculated as 0.38 μg/mL/unit of enzyme and the $IC_{50}$ for COX-2 was determined to be 0.84 μg/mL/unit.
Figure 8:
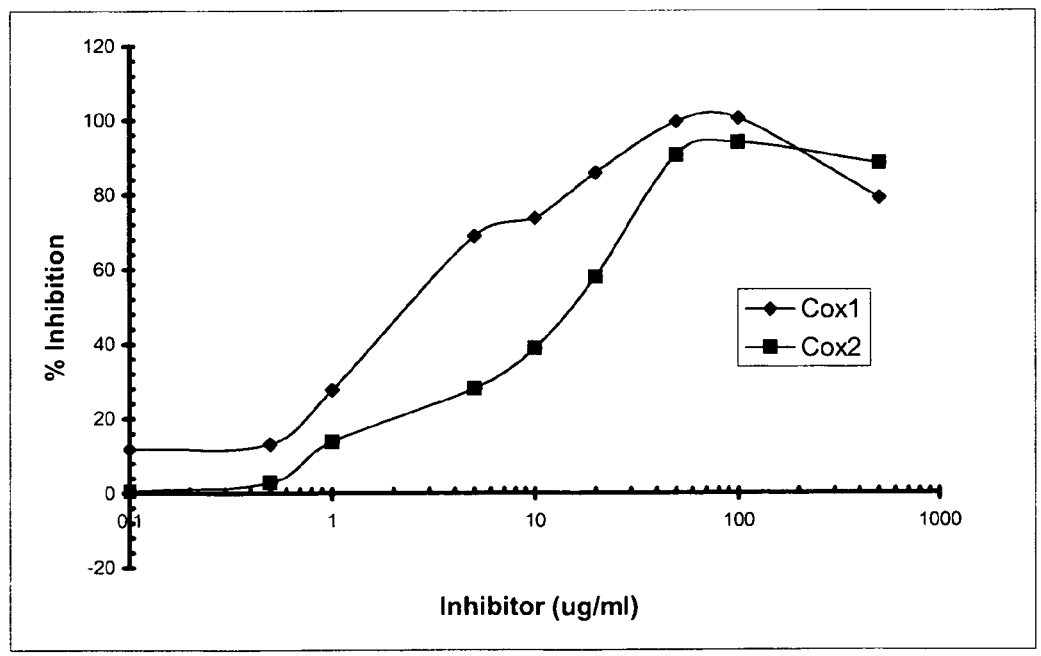
FIG. 8 depicts graphically a profile of the inhibition of COX-1 and COX-2 by a formulation produced by combining an extract of Free-B-Ring flavonoids isolated from the roots of S. baicalensis and an extract of flavans isolated from the bark of A. catechu in a ratio of about 20:80. The composition was examined for its inhibition of the peroxidase activity of recombinant ovine COX-1 (♦) and ovine COX-2 (■). The data is presented as percent inhibition vs. inhibitor concentration (μg/mL). The $IC_{50}$ of this composition for COX-1 was 0.18 μg/mL/unit of enzyme and the $IC_{50}$ for COX-2 was 0.41 μg/mL/unit.

The biochemical assay, used to measure inhibition of COX, relies on the protein's peroxidase activity in the presence of heme and arachidonic acid. This study which is described in Example 3 shows that the purified Free-B-Ring flavonoids, baicalin and baicalein isolated from *S. baicalensis* and the flavan extract isolated from *A. catechu*, and each individual standardized extract containing high concentrations of Free-B-Ring flavonoids and flavans inhibited COX activity (FIGS. 1-5). Additionally, compositions having different ratios of each of the individual standardized extracts (i.e., 80:20, 50:50 and 20:80 Free-B-Ring flavonoids:flavans), prepared as illustrated in Example 9, were all highly effective at inhibiting the COX activity in vitro (FIGS. 6-8).

It is also clearly demonstrated that the combination of Free-B-Ring flavonoids and flavans provides a more balanced modulation of the COX-1 and COX-2 enzymes. For example, aspirin, a COX-1 selective inhibitor, which is more than 150 times more potent against COX-1 than COX-2, causes gastrointestinal side effects. Conversely, Vioxx, celebrex and Bextra, which are selective COX-2 inhibitors having 50-200 times more potency against the COX-2 enzyme than the COX-1 enzyme, do not cause as much gastrointestinal damage, however, these COX-2 selective drugs increase cardiovascular risks. The formulation of Free-B-Ring flavonoids and flavans, on the other hand, provides a balance between the greater COX-2 activity of baicalin and the greater COX-1 activity of catechin. The moderate selectivity (2.3 fold) of catechin in the UP676 formulation against the COX-1 enzyme functions to reduce the cardiovascular risks caused by selective COX-2 inhibitors.

It is also significant that the mechanism of action is completely different between the currently available drugs referenced above and the natural formula—UP676. Aspirin, Vioxx, celebrex and Bextra irreversibly bind to the COX enzyme through covalent bonds to form tightly bound enzyme-inhibitor complexes. Such dramatic interaction completely changes the active site of the enzyme and the side pocket and destroys the enzyme. (Walker M C., Kurumbal R G., et al. (2001) Biochem. 357:709-718). The flavonoids in UP676, on the other hand, inhibit the COX enzyme through a weaker and reversible binding due to their antioxidant properties. In this interactive process, the structure and function of the COX enzyme are not irreversibly altered which results in a much better tolerance and safety profile for UP676.

Figure 9:
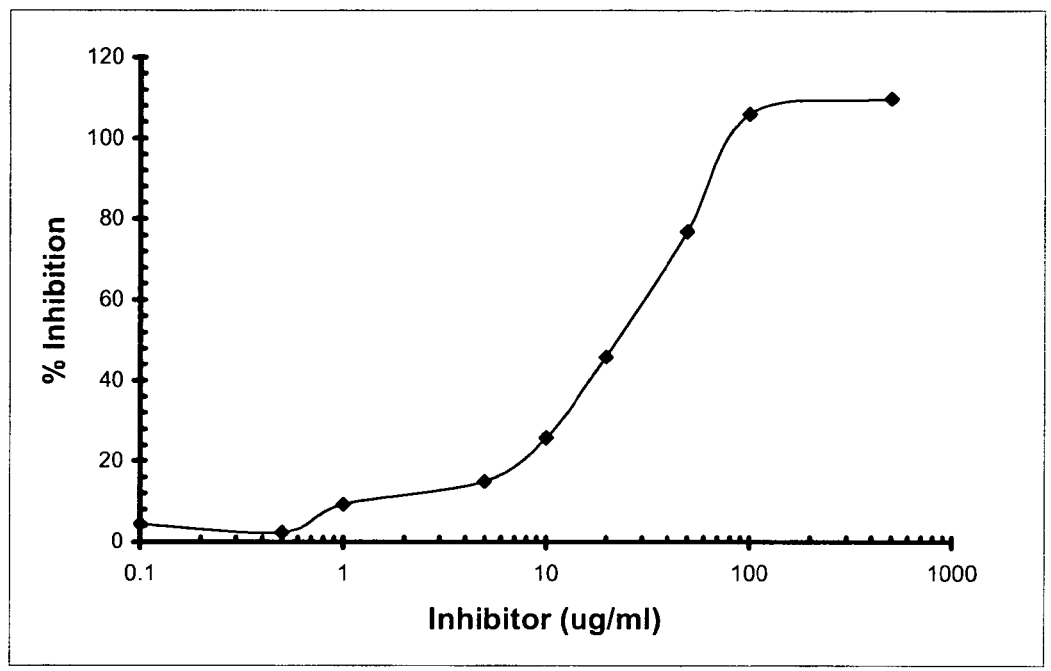
FIG. 9 depicts graphically a profile of the inhibition of 5-LO by the flavan extract from A. catechu. The composition was examined for its inhibition of recombinant potato 5-lipoxygenase activity (♦) as described in Example 4. The data is presented as percent inhibition of assays without inhibitor. The $IC_{50}$ for 5-LO was 1.38 μg/mL/unit of enzyme.
Figure 11:
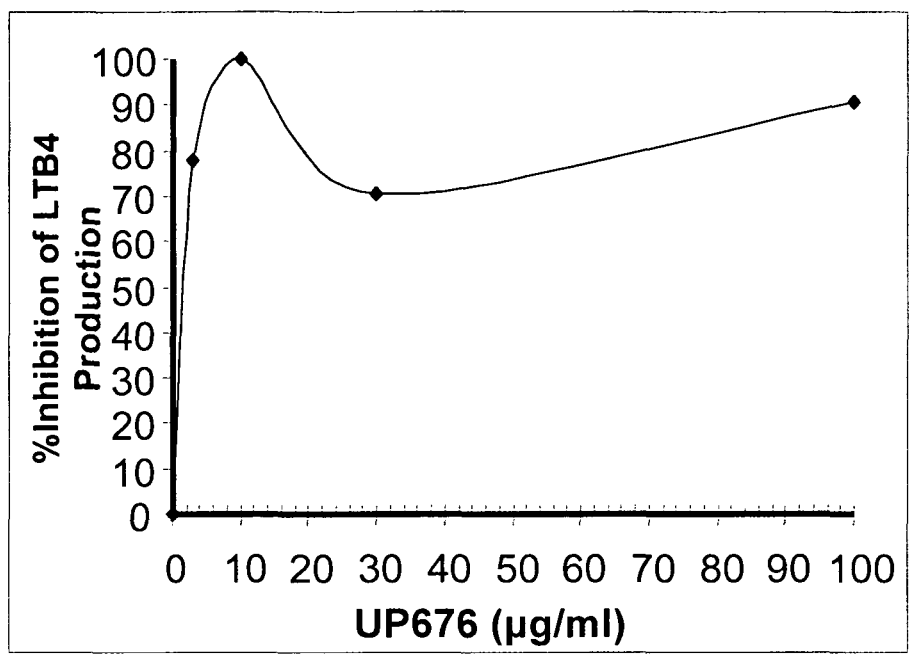
FIG. 11 depicts graphically the effect of increasing concentrations of UP676 on the amount of LPS-induced newly synthesized LTB$_4$ (♦) as determined by ELISA in THP-1 or HT-29 cells (ATCC) as described in Example 10. The UP676 was produced through the combination of standardized extracts of Free-B-Ring flavonoids isolated from the roots of *S. baicalensis* and flavans isolated from the bark of *A. catechu* in a ratio of 80:20. The activity of the UP676 formulation is expressed as % inhibition of induced LTB$_4$ synthesis.
Figure 12:
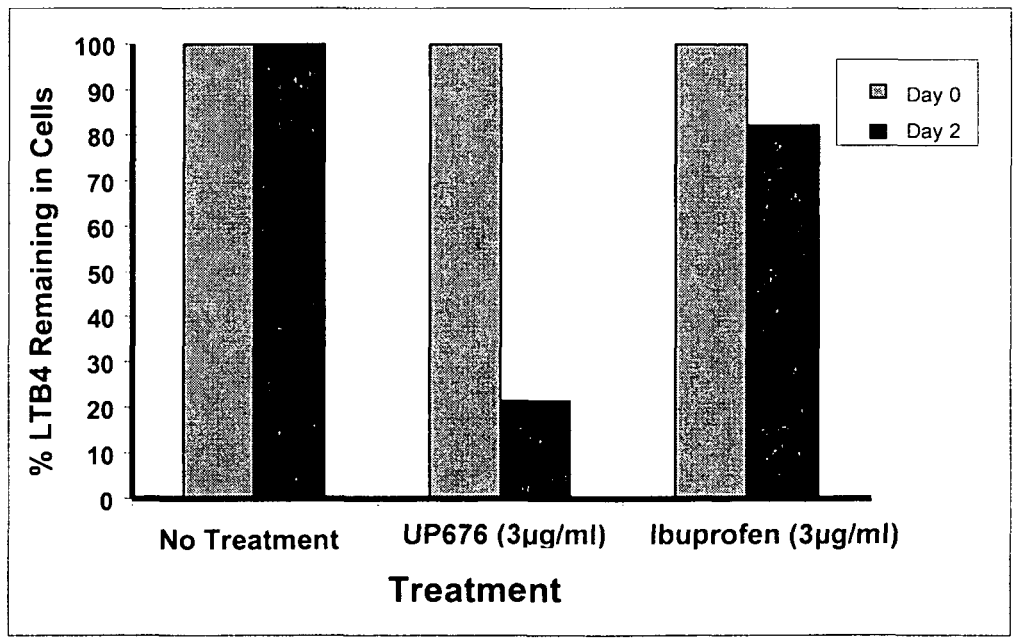
FIG. 12 compares the LTB$_4$ levels as determined by ELISA that remain in HT-29 cells after treatment with 3 μg/mL UP676 in non-induced cells to treatment with 3 μg/mL ibuprofen as described in Example 10. The UP676 formulation demonstrated 80% inhibition of LTB4 production in the HT-29 cells after two days of treatment.

The inhibition of LOX activity by a flavan extract isolated from *A. catechu*, was assessed using a lipoxygenase screening assay in vitro as described in Example 4. The results are illustrated in FIG. 9. Through the addition of flavans to the Free-B-ring flavonoids, UP676 also inhibits the activity of 5-LOX. The inhibition of 5-LOX results in a decrease in the accumulation of phagocytic leukotrienes, which are directly associated with the symptoms of chronic inflammation, and also reduces potential gastrointestinal side effects. Such efficacy is demonstrated in Example 10 and FIGS. 11 and 12. Briefly, cell assays that targeted inhibition of compounds in the breakdown of arachidonic acid in the LOX pathway, namely leukotriene B4 were performed using a UP676 sample as described in Example 10. The inhibition of $LTB_4$ by UP676 is illustrated in FIG. 12. With reference to the results illustrated by this Figure, it is evident that the combination of Free-B-Ring flavonoids with flavans provides the additional benefit of significantly reducing leukotriene production. This reduction in leukotriene production is by far superior to traditional non-steroidal anti-inflammatory drugs such as ibuprofen.

Example 11 demonstrates that UP676 effectively suppresses the gene expression of a group of pro-inflammatory cytokines, including IL-1β, TNFα and IL-6, in human cells. The experiments were conducted with the human peripheral blood mononuclear cells (PBMC) stimulated with lipopolysaccharide (LPS), which is a well-established inflammation cell model. When the cells were incubated with UP676 at various concentrations (0, 10, 30 and 100 μg/mL), the gene expression of the pro-inflammatory cytokines was suppressed in a dose dependent manner. (Table 12).

The pro-inflammatory cytokines, especially IL-1β, TNFα and IL-6, play key roles in chronic infections in the periodontium. They not only activate and recruit immune cells to the site of infection, but also induce loss of supporting bone and ligamentous attachment. It is well established that the mRNA levels of these cytokine genes are elevated in the diseased periodontium and the synthesis of the pro-inflammatory cytokines affects PDL cell phenotype and function. Since UP676 simultaneously suppresses pro-inflammatory cytokines dramatically, including IL-1β, TNFα and IL-6, at the mRNA level, it offers an effective way of treating periodontal diseases.

In vivo efficacy was demonstrated by the application of skin irritating substances, such as AA, to the ears and ankle joint of mice (to mimic the biological response of periodontal tissue to microbial infections and tooth plaques) and measuring the reduction of swelling in mice treated with UP676 as described in Example 12. The results are set forth in FIG. 13. With reference to this figure it can be seen that oral administration of UP676 at a dosage of 50 mg/kg to 200 mg/kg significantly reduces mouse ear swelling caused by local irritant.

Figure 14:
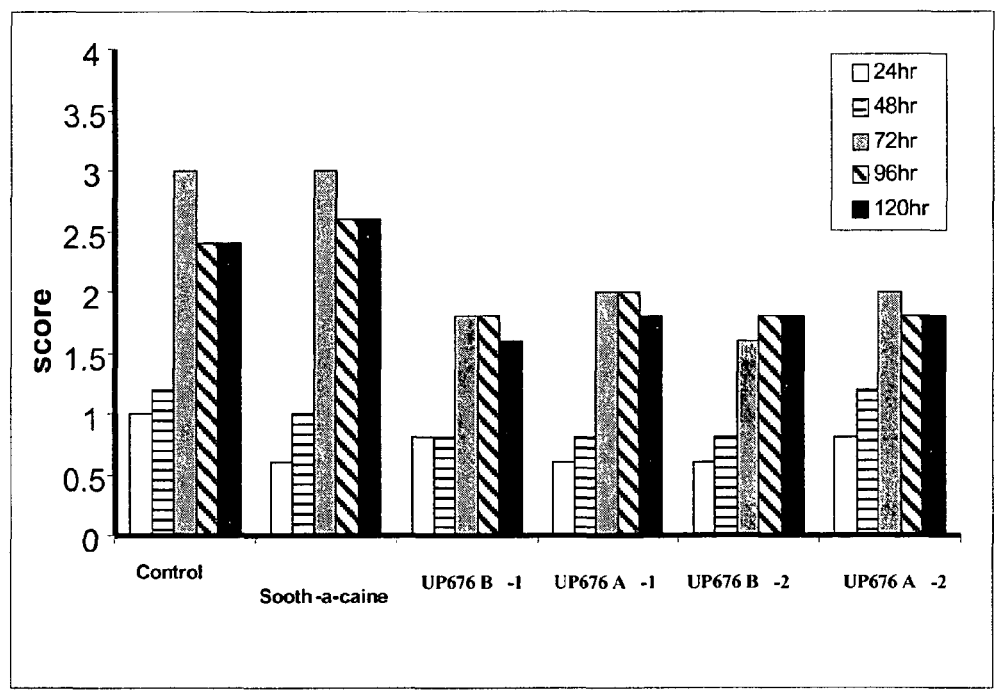
FIG. 14 depicts graphically the changes in hairless mice skin erythema scores in different treatment groups as a function of time following irradiation of the mice with UV light as described in Example 13. The mice in Groups B-1, A-1, B-2 and A-2 were treated with UP676 either before (Groups B-1 and B-2) or after (A-1 and A-2) irradiation. The UP676 was produced through the combination of standardized extracts of Free-B-Ring flavonoids isolated from the roots of *S. baicalensis* and flavans isolated from the bark of *A. catechu* in a ratio of 80:20.

The efficacy of topical application of UP676 was further demonstrated using another animal model by preventing and treating UV induced skin erythema as illustrated in Example 13 and FIG. 14. In the study described in Example 13, UP676 in a blend ratio of 80:20 Free-B-Ring flavonoids:flavans was dissolved in water and applied topically at two concentration to the skin of hairless mice both before and after UV exposure, respectively. The erythema scores of the hairless mice from four UP676 groups, in both concentrations and regardless the applications time as before or after UV exposure, all showed much less redness in smaller skin areas as compared to severe and extended erythema in both the control group and the group that was treated with Sooth-A Cain. This study demonstrates that UP676 can penetrate into the skin of hairless mice to reduce the inflammatory response. While not limited by theory it is believed that this result is achieved by the simultaneous inhibition of both the eicosanoid and cytokine pathways.

Example 14 (Table 13) describes a general method for the preparation of a UP676 cream using pharmacologically, dermatologically and cosmetic acceptable excipients. For purposes of illustration this Example provides a detailed procedure for the preparation of a 0.5 wt % UP676 topical cream. The compositions of the present invention can also be formulated as pharmaceutical compositions, which include other components such as a pharmaceutically and/or cosmetically acceptable excipient, an adjuvant, flavors, and/or a carrier. For example, compositions of the present invention can be formulated in an excipient that the host to be treated can tolerate. An excipient is an inert substance used as a diluent or vehicle for a drug. Examples of such excipients include, but are not limited to water, alcohols (ethanol or ethylene glycol, propylene glycol), buffers, saline, hydrated silica, dextrose solution, cellulose gum, sorbitol, mannitol, preservatives and other aqueous physiologically balanced salt solutions. The therapeutic composition can also contain minor amounts of additives, such as substances that enhance isotonicity and chemical stability. As illustrated in Example 17, such preservatives include but are not limited to BHA, BHT, diammonium citrate (DAC), butylated hydroxytoluene, ethylenediamine tetraacetic acid (EDTA), $H_2O_2$, propyl gallate (PG), sodium gluconate (SG), and sodium bisulfate/metabisulfite (SBS), sodium lauryl sulfate, stannous chloride, stannous fluoride, sodium benzoate, benzoic acid. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, xanthan gum, methyl cellulose, or dextran. Examples of buffers include phosphate buffer, bicarbonate buffer, tris buffer, histidine, citrate, and glycine, or mixtures thereof, while examples of preservatives include, but are not limited to thimerosal, m- or o-cresol, formalin and benzyl alcohol. Standard formulations can either be liquid or gel or paste, or solids, which can be taken up in a suitable format as a suspension or solution for administration.

In one embodiment, the composition is prepared as a controlled release formulation, which slowly releases the composition of the present invention into the host. As used herein, a controlled release formulation comprises a composition of the present invention in a controlled release vehicle. Suitable controlled release vehicles will be known to those skilled in the art. Preferred controlled release formulations are biodegradable (i.e., bioerodible).

Figure 15:
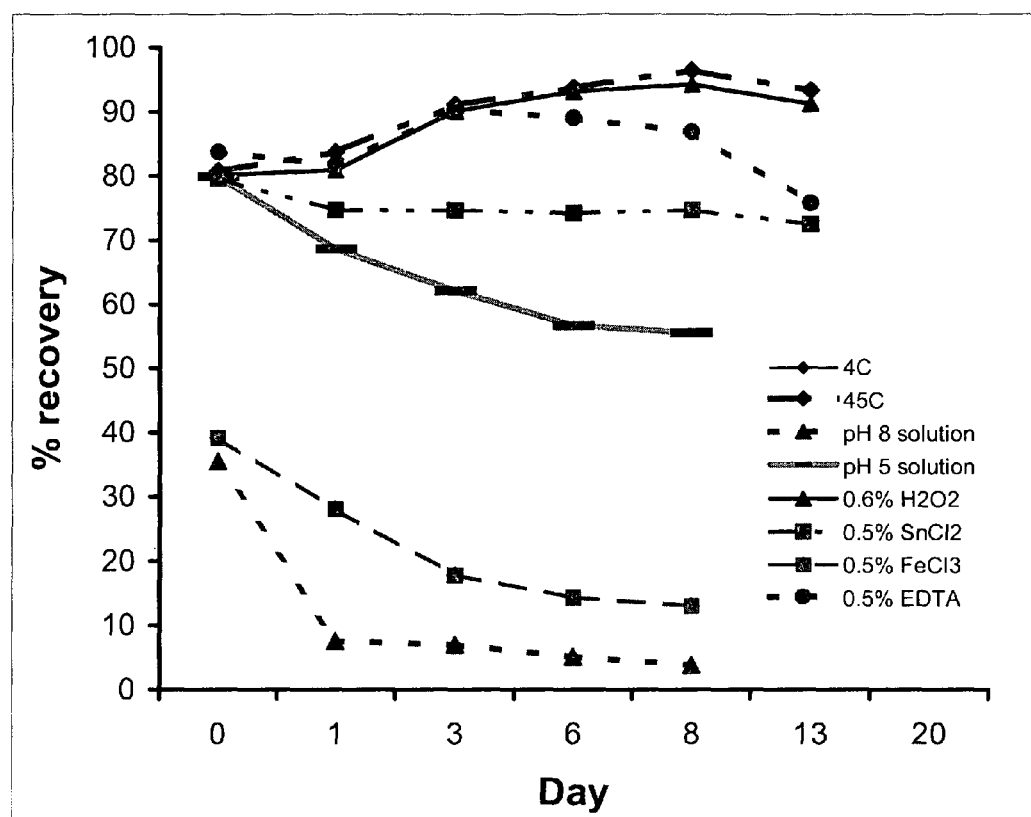
FIG. 15 depicts graphically the change in concentration of pure catechin in various aqueous solutions on days 1, 3, 6, 8 and 13 under the conditions set forth in Example 15.
Figure 16:
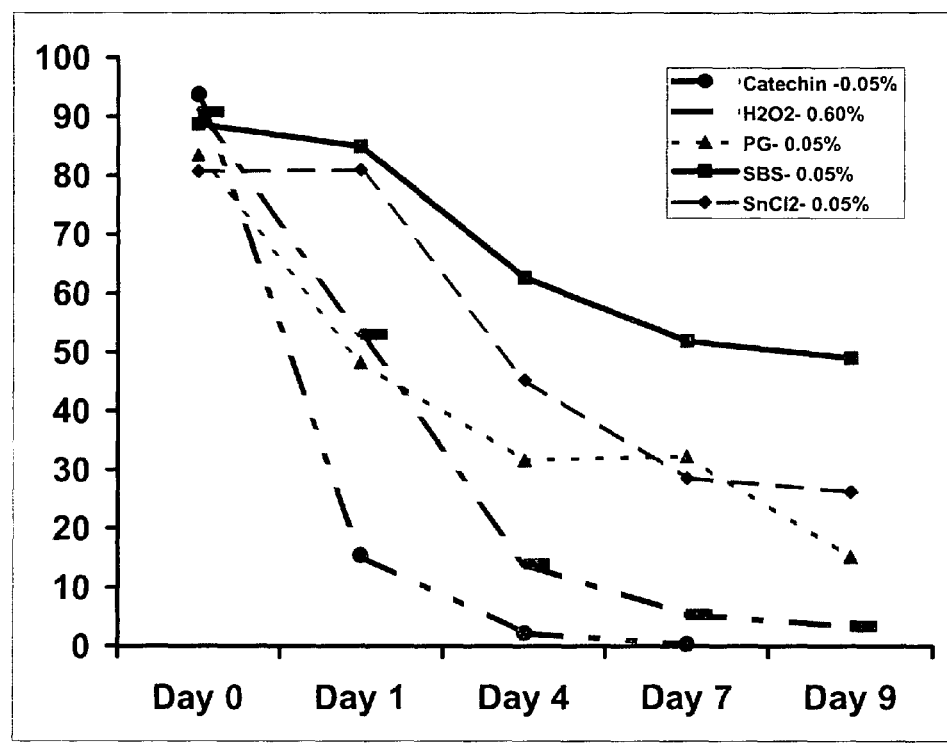
FIG. 16 depicts graphically various chemical preservatives that can be used to protect pure catechin in aqueous solution at a pH 7.5 from decomposition and color change.

Example 15 illustrates the stability of catechin in solution varying both pH and preservatives. Catechin contains four phenolic hydroxyl groups which makes this compound more acidic and sensitive to oxidative stress. The extremely high Oxygen Radical Absorption Capacity (ORAC at 20,000) of catechin demonstrates its antioxidant properties. Based upon the stress test of pure catechin under varying conditions, such as pH, existence of $H_2O_2$ and metal ions, it was determined as illustrated in FIG. 15, that catechin is stable under neutral conditions at both 4° C. and 40° C., but not under basic conditions or when exposed to metal ions, such as $Fe^{3+}$. Even under weakly basic conditions (pH=7.5) catechin decomposes. However, it can be preserved by a number of preservatives, including but not limited to stannous chloride ($SnCl_2$), sodium bisulfate/metabisulfite (SBS), and other preservatives as illustrated FIG. 16.

Another advantage of combining these two classes of compounds is that in the preferred embodiment, the formulation of significant amounts of Free-B-Ring flavonoids (80% by weight) with comparatively lower concentrations of flavans (20% by weight), the more potent anti-oxidative flavans function as natural preservatives against oxidative degradation and act as neutralization and buffering agent in the formula to deliver the major active components—Free-B-Ring flavonoids at the optimum pH and ionization conditions.

Figure 17:
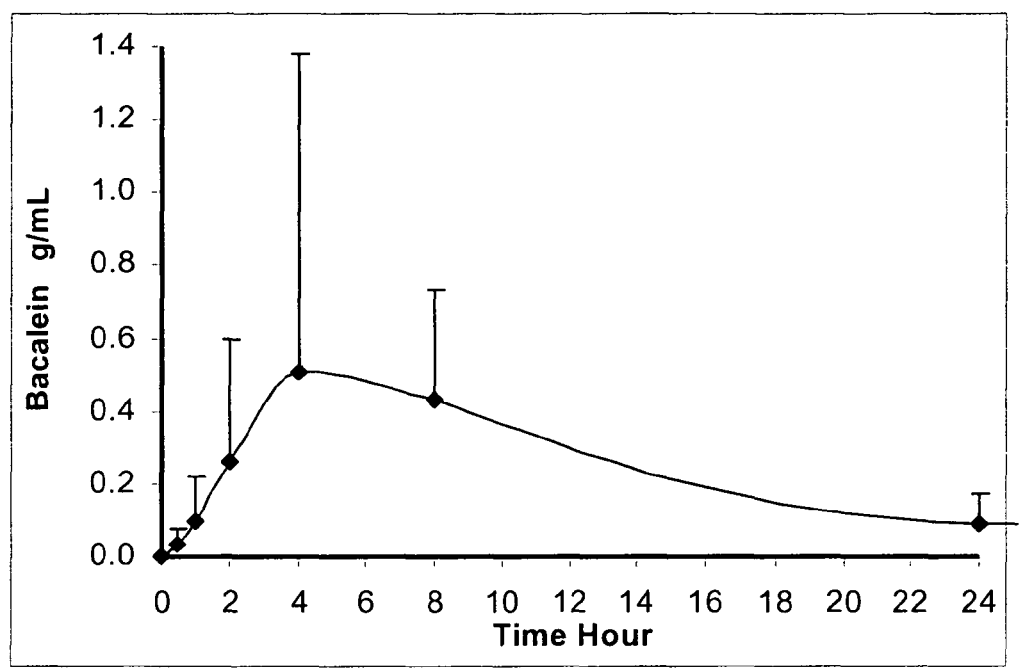
FIG. 17 depicts graphically the average serum Free-B-Ring flavonoid concentration against time from ten healthy subjects (n=10, 6 female and 4 male) after oral administration of a single dose of 300 mg UP676. The average $C_{max}$ was 0.93 μg/mL (% RSD=84.9) and the average $T_{max}$ was approximately 5.8 hours (% RSD=43.4).

Example 16 illustrates the bioavailability of the active components in UP676 after oral administration in humans. The results are set forth in FIG. 17. With reference to FIG. 17, the wide error bars seen in this analysis are due to individual variation between subjects. Gender and differences in weight did not correlate with the differences seen for $C_{max}$ and $T_{max}$ or absorption and clearance. It is clearly demonstrated that Free-B-Ring flavonoids in UP676 can penetrate through epithelium cells. However, the existence of Free-B-Ring flavonoids in human body fluids, such as serum is not in the aglycone form such as baicalein, but rather conjugated structures such as baicalin or sulfurated baicalein. To quantify the total concentration of Free-B-Ring flavonoids in serum, all of the conjugated compounds were hydrolyzed using two enzymes to release the aglycone—baicalein which was then quantified by HPLC.

Table 14 shows the maximal values found for baicalein concentration ($C_{max}$, μg/mL) and time ($T_{max}$, hour) at which they were observed for each subject. The data shows that for most subjects, the maximum concentration was achieved between 4 and 8 hours after the initial dose. The average $C_{max}$ was 0.93 μg/mL (% RSD=84.9) and the average $T_{max}$ was approximately 5.8 hours (% RSD=43.4). Based on this data, the average time for absorption and clearance was calculated and plotted for the entire study group (FIG. 17). Since the $IC_{50}$ values of COX inhibition from UP676 are between 0.2-0.4 μg/mL as shown in the FIG. 6, it takes about two hours after oral administration for UP676 to reach efficacious concentrations. However, serum concentration of the Free-B-Ring flavonoids will remain above therapeutic levels for approximately 10 hours after oral administration. To compensate for the lack of quick bioavailability from Free-B-Ring flavonoids, the formulation of catechin type flavans offers a complimentary benefit. Studies of the bioavailability of catechins, quercetin, and epigallocatechin-3-gallate (Kao et al. (2000) Endocrinology 141(3):980-987; Koga and Meydani (2001) Am. J. Clin. Nutr. 73:941-948; Lee et al. (2002) Cancer Epidemiol. Biomarker Prevention 11:1025-1032) show that the $C_{max}$ and $T_{max}$ of catechin occur quickly (about 45 minutes) and the half life was reported to be 2 hours. Therefore, by combining Free-B-Ring-flavonoids with flavans, the quickly penetrating catechins reach efficacious serum concentrations in about 0.5 hour after oral administration. When the catechin concentration drops, the second active component, the Free-B-Ring flavonoids reach bioactive concentrations that will last up to 12 hours after oral administration. In conclusion, the UP676 formulation was designed to have quick on-site periodontal pain reduction and anti-inflammatory effects resulting from the flavans, such as catechin and longer lasting effects resulting from the Free-B-Ring flavonoids, such as baicalin. Such synergistic and complimentary effects will also be realized via topical delivery of the formula.

Example 17 illustrates the safety of topically applying UP676 to human skin. The formulated UP676 as illustrated in Examples 9 and 14 was evaluated on human skin for potential irritation and induction of contact sensitization. A total of 97 and 101 subjects completed induction and challenge with the 0.5% and 1.5% UP676 creams, respectively. Test results show that UP676 creams at 0.5% and 1.5% concentration produce minimal irritation and do not elicit evidence of induced contact sensitization.

In conclusion, the compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of a mixture of Free-B-Ring flavonoids and flavans synthesized and/or isolated from a single plant or multiple plants. In a one embodiment the composition is administered topically. The therapeutic agents of the instant invention are administered topically by any suitable means, known to those of skill in the art for topically administering therapeutic compositions including, but not limited to as a paste, ointment, gel, lotion, or mouse rinse liquid, or cream base or as an emulsion, as a patch, dressing or mask, a nonsticking gauze, a bandage, a swab or a cloth wipe. Such topical application can be locally administered to any affected area, using any standard means known for topical administration, such as brushing with a toothbrush, coated on dental floss, or applying with a swab or rinsing with the liquid or gel. A therapeutic composition can be administered in a variety of unit dosage forms depending upon the method of administration. For particular modes of delivery, a therapeutic composition of the present invention can be formulated in an excipient of the present invention. A therapeutic reagent of the present invention can be administered to any host, preferably to mammals, and more preferably to humans. The particular mode of administration will depend on the condition to be treated.

In one embodiment, a suitable ointment is comprised of the desired concentration of the mixture of Free-B-Ring flavonoids and flavans, that is an efficacious, nontoxic quantity generally selected from the range of 0.001% to 100% based on total weight of the topical formulation, from 0.05 to 5% (preferably 0.1 to 0.5%) of toothpaste, from 0.01 to 5% of mouse washing liquid (preferably 0.2 to 1%), and from 0.1 to 25% (preferably 0.5 to 5%) of emulsion gel or cream.

Regardless of the manner of administration, the specific dose is calculated according to the approximate body weight of the host. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data.

It should be noted that the invention described herein may be used for veterinary as well as human applications and that the term "host" should not be construed in a limiting manner. In the case of veterinary applications, the dosage ranges can be determined as described above, taking into account the body weight of the animal.

The following examples are provided for illustrative purposes only and are not intended to limit the scope of the invention.

EXAMPLES

Example 1

Preparation of Organic and Aqueous Extracts from *Acacia* and *Scuttellaria* Plants Plant material from *Acacia catechu* (L) Willd. barks, *Scutellaria orthocalyx* roots, *Scutellaria baicalensis* roots or *Scutellaria lateriflora* whole plant and various *Oroxylum* and *Uncaria* species was ground to a particle size of no larger than 2 mm. Dried ground plant material 60 g) was then transferred to an Erlenmeyer flask and methanol:dichloromethane (1:1) (600 mL) was added. The mixture was shaken for one hour, filtered and the biomass was extracted again with methanol: dichloromethane (1:1) (600 mL). The organic extracts were combined and evaporated under vacuum to provide the organic extract (see Table 1 below). After organic extraction, the biomass was air dried and extracted once with ultra pure water (600 mL). The aqueous solution was filtered and freeze-dried to provide the aqueous extract (see Table 1 below).

TABLE 1

Yield of Organic and Aqueous Extracts from Plant Species

| Plant Source | Plant Part | Organic Extract | Aqueous Extract |
| --- | --- | --- | --- |
| Acacia catechu | barks | 27.2 g | 10.8 g |
| Scutellaria orthocalyx | roots | 4.04 g | 8.95 g |
| Scutellaria baicalensis | roots | 9.18 g | 7.18 g |
| Scutellaria lateriflora | whole plant | 6.54 g | 4.08 g |
| Oroxylum indicum | seeds | 6.58 g | 4.04 g |
| Uncaria hirsuta | arerial parts | 2.41 g | 0.90 g |
| Uncaria sinensis | arerial parts | 3.94 g | 1.81 g |
| Uncaria tomentosa | bark | 6.47 g | 2.31 g |

Example 2

Inhibition of COX-2 and COX-1 Peroxidase Activity by Plant Extracts from *A. catechu*, Various *Scutellaria* Species and Other Plants The bioassay directed screening process for the identification of specific COX-2 inhibitors was designed to assay the peroxidase activity of the enzyme as described below.

Peroxidase Assay. The assay to detect inhibitors of COX-2 was modified for a high throughput platform (Raz). Briefly, recombinant ovine COX-2 (Cayman) in peroxidase buffer (100 mM TBS, 5 mM EDTA, 1 µM Heme, 1 mg epinephrine, 0.094% phenol) was incubated with extract (1:500 dilution) for 15 minutes. Quantablu (Pierce) substrate was added and allowed to develop for 45 minutes at 25° C. Luminescence was then read using a Wallac Victor 2 plate reader. The results are presented in Table 2.

Table 2 sets forth the inhibition of the COX-2 enzyme by the organic (20 µg/mL) and aqueous (20 µg/mL) extracts obtained from three plant species, including the bark of *A. catechu*, roots of two *Scutellaria* species, which are comprised of structurally similar Free-B-Ring flavonoids. Data is presented as the percent of peroxidase activity relative to the recombinant ovine COX-2 enzyme and substrate alone. The percent inhibition by the organic extract ranged from 30% to 90%.

TABLE 2

Inhibition of COX-2 Peroxidase Activity by Various Species

| Plant Source | Inhibition of COX-2 by organic extract | Inhibition of COX-2 by aqueous extract |
|---|---|---|
| Acacia catechu (bark) | 75% | 30% |
| Scutellaria orthocalyx (root) | 55% | 77% |
| Scutellaria baicalensis (root) | 75% | 0% |

Comparison of the relative inhibition of the COX-1 and COX-2 isoforms requires the generation of $IC_{50}$ values for each of these enzymes. The $IC_{50}$ is defined as the concentration at which 50% inhibition of enzyme activity in relation to the control is achieved by a particular inhibitor. In these experiments, $IC_{50}$ values were found to range from 6 to 50 µg/mL and 7 to 80 µg/mL for the COX-2 and COX-1 enzymes, respectively, as set forth in Table 3. Comparison of the $IC_{50}$ values of COX-2 and COX-1 demonstrates the specificity of the organic extracts from various plants for each of these enzymes. The organic extract of S. lateriflora for example, shows preferential inhibition of COX-2 over COX-1 with $IC_{50}$ values of 30 and 80 µg/mL, respectively. While some extracts demonstrate preferential inhibition of COX-2, others do not. Examination of the HTP fractions and purified compounds from these fractions is necessary to determine the true specificity of inhibition for these extracts and compounds.

TABLE 3

$IC_{50}$ Values of Organic Extracts for Human and Ovine COX-2 and COX-1

| Plant Source | $IC_{50}$ Human COX-2 (µg/mL) | $IC_{50}$ Ovine COX-2 (µg/mL) | $IC_{50}$ Ovine COX-1 (µg/mL) |
|---|---|---|---|
| Acacia catechu (bark) | 3 | 6.25 | 2.5 |
| Scutellaria orthocalyx (root) | Not tested | 10 | 10 |
| Scutellaria baicalensis (root) | 30 | 20 | 20 |
| Scutellaria lateriflora (whole plant) | 20 | 30 | 80 |
| Uncaria sinensis (whole plant) | Not tested | 2.2 | 72.0 |
| Oroxylum indicum (seeds) | Not tested | 2.48 | 8.4 |

Example 3

Inhibition of COX-1 and COX-2 Peroxidase Activity

In order to screen for compounds that inhibited the COX-1 and COX-2 activities, a high throughput, in vitro assay was developed that utilized the inhibition of the peroxidase activity of both enzymes. (Needleman et al. (1986) Annu Rev Biochem. 55:69). Briefly, the composition or compound being examined was titrated against a fixed amount of COX-1 and COX-2 enzymes. A cleavable, peroxide chromophore was included in the assay to visualize the peroxidase activity of each enzyme in presence of arachidonic acid as a cofactor. Typically, assays were performed in a 96-well format. Each inhibitor, taken from a 10 mg/mL stock solution in 100% DMSO, was tested in triplicate at room temperature using the following range of concentrations: 0, 0.1, 1, 5, 10, 20, 50, 100, and 500 µg/mL. To each well, 150 µL of 100 mM Tris-HCl, pH 7.5 was added along with 10 µL of 22 µM Hematin diluted in tris buffer, 10 µL of inhibitor diluted in DMSO and 25 units of either the COX-1 or COX-2 enzyme. The components were mixed for 10 seconds on a rotating platform, followed by the addition of 20 µL of 2 mM N,N,N'N'-tetramethyl-p-phenylenediamine dihydrochloride (TMPD) and 20 µL of 1.1 mM arachidonic acid to initiate the reaction. The plate was shaken for 10 seconds and then incubated 5 minutes before reading the absorbance at 570 nm. The inhibitor concentration vs. % inhibition was plotted and the $IC_{50}$ determined by taking the half-maximal point along the isotherm and intersecting the concentration on the X-axis. The $IC_{50}$ was then normalized to the number of enzyme units in the assay. The COX-1/COX-2 inhibitory activity from 20 µg/mL of pure Free-B-Ring flavanoids are summarized in Table 4.

TABLE 4

Inhibition of COX Enzyme Activity by Purified Free-B-Ring Flavonoids

| Free-B-Ring Flavonoids | Inhibition of COX-1 | Inhibition of COX-2 |
|---|---|---|
| Baicalin | 95% | 97% |
| Baicalein | 107% | 109% |
| 5,6-Dihydroxy-7-methoxyflavone | 75% | 59% |
| 7,8-Dihydroxyflavone | 74% | 63% |
| Wogonin | 16% | 12% |

Figure 2:
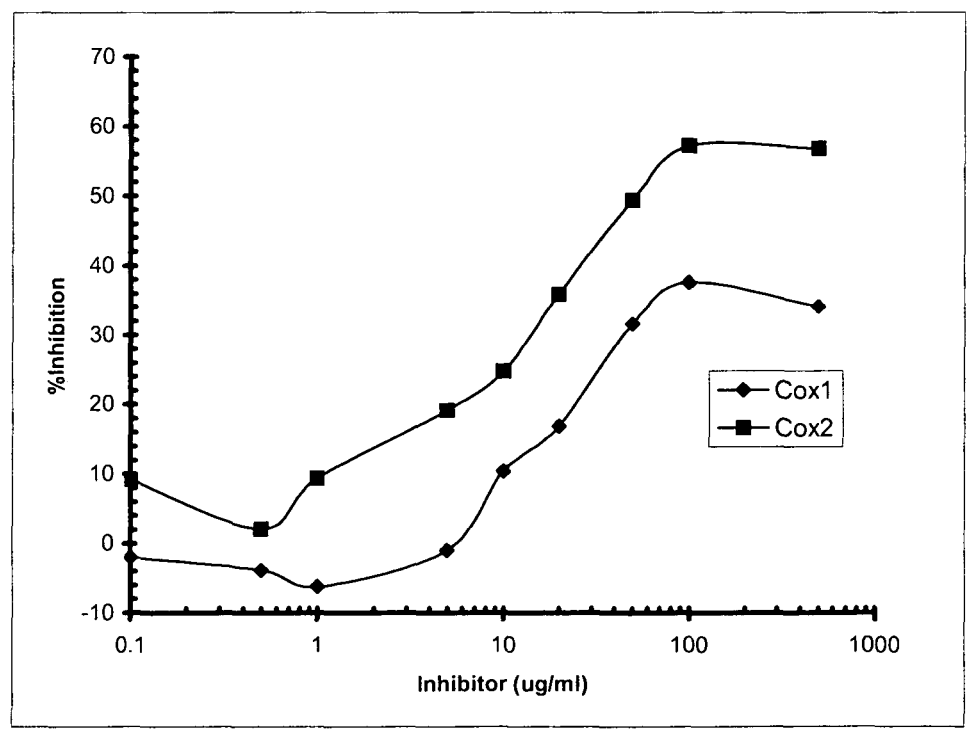
FIG. 2 depicts graphically a profile of the inhibition of COX-1 and COX-2 by the purified component baicalin, which was isolated from S. baicalensis. The compound was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was determined to be 0.44 μg/mL/unit of enzyme and the $IC_{50}$ for COX-2 was determined to be 0.28 μg/mL/unit.
Figure 3:
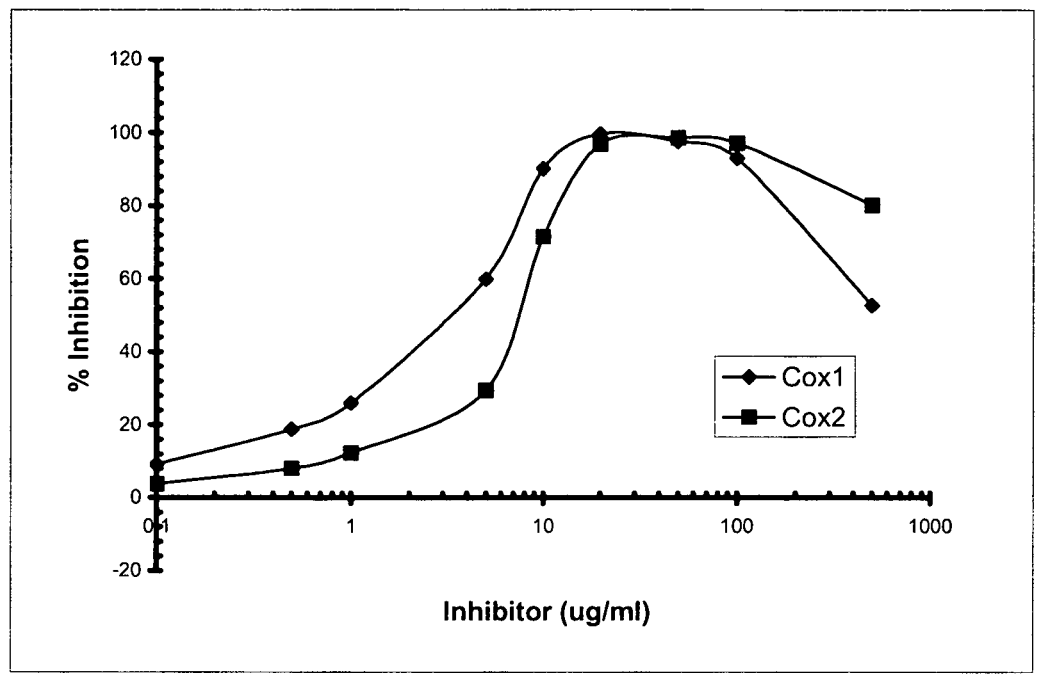
FIG. 3 depicts graphically a profile of the inhibition of COX-1 and COX-2 by the purified component baicalein isolated from S. baicalensis. The compound was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was determined to be 0.18 μg/mL/unit of enzyme and the $IC_{50}$ for COX-2 was determined to be 0.28 μg/mL/unit.
Figure 4:
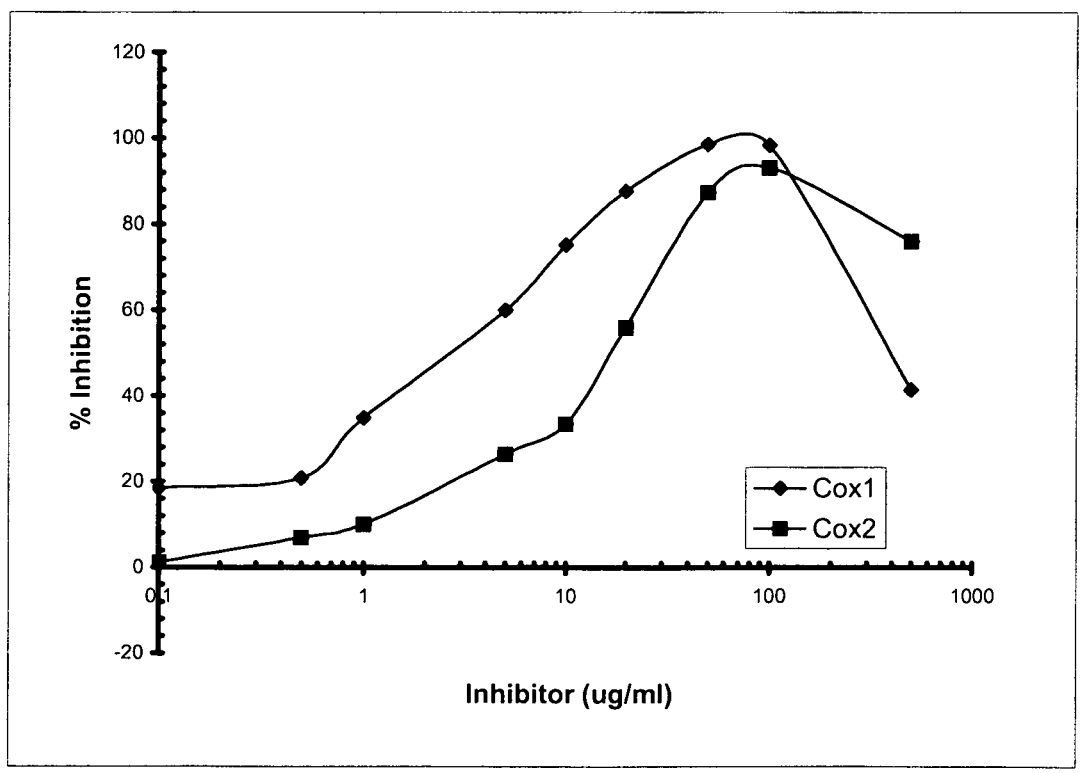
FIG. 4 depicts graphically a profile of the inhibition of COX-1 and COX-2 by a standardized flavan extract containing 50% total flavans, which was isolated from A. catechu. The extract was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was calculated as 0.17 μg/mL/unit of enzyme and the $IC_{50}$ for COX-2 was calculated as 0.41 μg/mL/unit.
Figure 5:
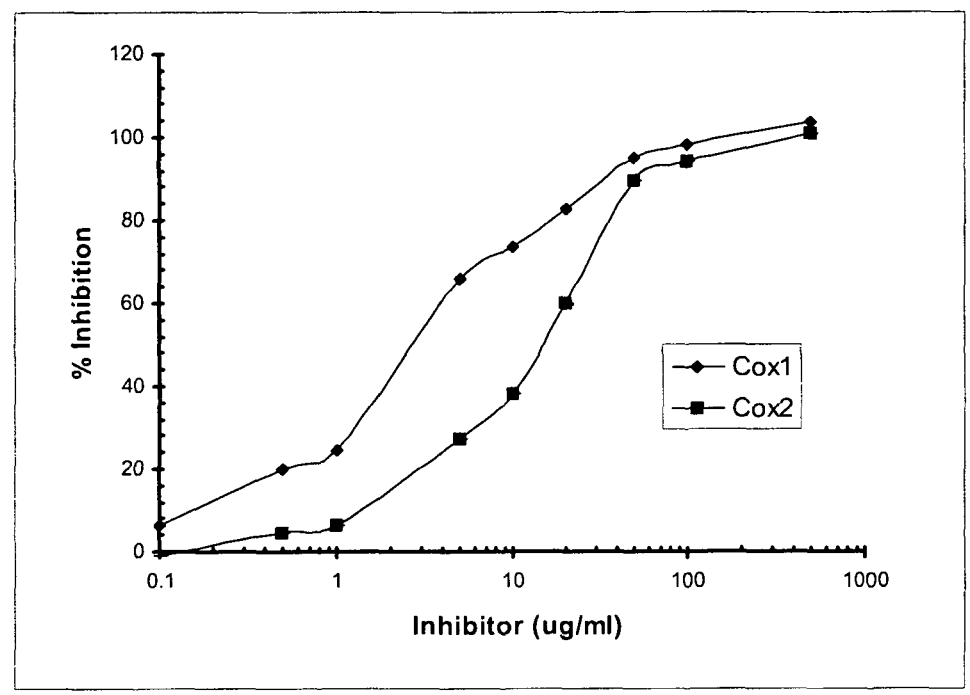
FIG. 5 depicts graphically a profile of the inhibition of COX-1 and COX-2 by a composition of matter comprised of greater than 90% flavans isolated from A. catechu. The composition was examined for its inhibition of the peroxidase activity of recombinant ovine COX-1 (♦) and ovine COX-2 (■). The data is presented as percent inhibition vs. inhibitor concentration (μg/mL). The $IC_{50}$ for COX-1 was calculated as 0.11 μg/mL/unit of enzyme and the $IC_{50}$ for COX-2 was calculated as 0.42 μg/mL/unit.

The dose responses and $IC_{50}$ values for a standardized Free-B-Ring flavonoid extract, baicalin, and baicalein isolated from the roots of S. baicalensis are provided in FIGS. 1, 2 and 3, respectively. The dose responses and $IC_{50}$ values for two standardized flavan extract (50% and >90% flavans, respectively) isolated from the heartwood of Acacia catechu are provided in FIGS. 4 and 5, respectively. The dose responses and $IC_{50}$ values for three formulations of Free-B-Ring flavonoids and flavans of varying composition are provided in FIG. 6 (80:20 blending), FIG. 7 (50:50 blending) and FIG. 8 (20:80 blending), respectively.

Example 4

Inhibition of 5-Lipoxygenase by Catechin Isolated from A. catechu

One of the most important pathways involved in the inflammatory response is produced by non-heme, iron-containing lipoxygenases (5-LO, 12-LO, and 15-LO), which catalyze the addition of molecular oxygen onto fatty acids such as AA (AA) to produce the hydroperoxides 5-, 12- and 15-HPETE, which are then converted to leukotrienes. There were early indications that the flavan extract from A. catechu may provide some degree of LOX inhibition, thereby preventing the formation of 5-HPETE. A Lipoxygenase Inhibitor Screening Assay Kit (Cayman Chemical, Inc., Cat#760700) was used to assess whether an extract isolated from A. catechu containing >90% flavans directly inhibited LOX in vitro. The 15-LO from soybeans normally used in the kit was replaced with potato LOX, after a buffer change from phosphate to a tris-based buffer using microfiltration was performed. This assay detects the formation of hydroperoxides through an oxygen sensing chromagen. Briefly, the assay was performed in triplicate by adding 90 µL of 0.17 units/µL potato 5-LO, 20 µL of 1.1 mM AA, 100 µL of oxygen-sensing chromagen and 10 µL of purified flavan inhibitor to final concentrations ranging from 0 to 500 µg/mL. The $IC_{50}$ for 5-LO inhibition from this composition was determined to be 1.38 µg/mL/unit of enzyme. The results are set forth in FIG. 9.

Example 5

HPLC Quantification of Free-B-Ring Flavonoids in Active Extracts Isolated from *Scutellaria orthocalyx* (Roots) and *Scutellaria baicalensis* (Roots)

The presence and quantity of Free-B-Ring flavonoids in five active extracts isolated from three different plant species as described in Examples 1 and 2 were determined by HPLC and the results are set forth in the Table 5, below. The Free-B-Ring flavonoids were quantitatively analyzed by HPLC on a Luna C-18 column (250×4.5 mm, 5 μm) using a 1% phosphoric acid and acetonitrile gradient from 80% to 20% in 22 minutes. The Free-B-Ring flavonoids were detected using a UV detector at 254 nm and identified based on retention time by comparison with baicalin, baicalein and other Free-B-Ring flavonoid standards.

TABLE 5

Free-B-Ring Flavonoid Content in Active Plant Extracts

| Active Extracts | Weight of Extract | % Extractible from BioMass | Total amount of Free-B-Ring Flavonoids | % Free-B-Ring Flavonoids in Extract |
|---|---|---|---|---|
| S. orthocalyx (aqueous extract) | 8.95 g | 14.9% | 0.2 mg | 0.6% |
| S. orthocalyx (organic extract) | 3.43 g | 5.7% | 1.95 mg | 6.4% |
| S. baicalensis (aqueous extract) | 7.18 g | 12.0% | 0.03 mg | 0.07% |
| S. baicalensis (organic extract) | 9.18 g | 15.3% | 20.3 mg | 35.5% |

Example 6

HPLC Quantification of Active Extracts from *Acacia catechu*

The flavans in the organic and aqueous extracts isolated from *Acacia catechu* as illustrated in Examples 1 and 2 were quantified by HPLC using a PhotoDiode Array detector (HPLC/PDA) and a Luna C18 column (250 mm×4.6 mm). The flavans were eluted from the column using an acetonitrile gradient from 10% to 30% ACN over a period of 20 minutes, followed by 60% ACN for five minutes. The results are set forth in Table 6. The flavans were quantified based on retention time and PDA data using catechin and epicatechin as standards. The retention times for the two major flavans were 12.73 minutes and 15.76 minutes, respectively.

TABLE 6

Catechin Content in Active Plant Extracts

| Active Extracts from bark of A. catechu | Weight of Extract | % Extractible from BioMass | % Flavans in Extract |
|---|---|---|---|
| Aqueous Extract | 10.8 g | 18.0% | 0.998% |
| Organic Extract | 27.2 g | 45.3% | 30.37% |

Example 7

Preparation of a Standardized Extract from *A. catechu*

*A. catechu* (500 mg of ground root) was extracted twice with 25 mL (2×25 mL) of the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The two extracts from each individual extraction were combined concentrated and dried under low vacuum. The identification of the chemical components in each extract was achieved by HPLC using a PhotoDiode Array detector (HPLC/PDA) and a 250 mm×4.6 mm C18 column. The chemical components were quantified based on retention time and PDA data using catechin and epicatechin as standards. The results are set forth in Table 7. As shown in Table 7, the flavan extract generated from solvent extraction with 80% methanol/water provided the highest concentration of flavan components.

TABLE 7

Solvents for Generating Standardized Flavan Extracts from *A. catechu*

| Extraction Solvent | Weight of Extract | % Extractible from BioMass | Total amount of Catechins | % Catechins in Extract |
|---|---|---|---|---|
| 100% water | 292.8 mg | 58.56% | 13 mg | 12.02% |
| water:methanol (80:20) | 282.9 mg | 56.58% | 13 mg | 11.19% |
| water:methanol (60:40) | 287.6 mg | 57.52% | 15 mg | 13.54% |
| water:methanol (40:60) | 264.8 mg | 52.96% | 19 mg | 13.70% |
| water:methanol (20:80) | 222.8 mg | 44.56% | 15 mg | 14.83% |
| 100% methanol | 215.0 mg | 43.00% | 15 mg | 12.73% |
| methanol:THF (80:20) | 264.4 mg | 52.88% | 11 mg | 8.81% |
| methanol:THF (60:40) | 259.9 mg | 51.98% | 15 mg | 9.05% |

A standardized extract was obtained from whole plant of *Uncaria gambir* by extracting the biomass with alcohol/water solvent. The flavan content in the standardized extract from *Uncaria gambir* were quantified using the same method. The results are set forth in Table 8. The flavans were quantified based on retention time and PDA data using catechin as standards.

Higher purity material can be obtained by recrystallization of extracts having a catechin content of between 8%-15% using an alcohol/water and/or aqueous solvents as the recrystallization solvent. It may be necessary to decolorize prior to recrystallization by adding active charcoal or other decolorization agent to a heated saturated solution of the extract. The high purity catechins then crystallized upon cooling of the heated saturated solution. The crystals were then filtered to remove solvent, dried and ground into a fine powder. Recrystallization can be repeated as necessary to achieve the desired level of purity (60%-100% of catechin flavans).

Example 8

Preparation of Standardized Free-B-Ring Flavonoid Extracts from Various *Scutellaria* Species

*S. orthocalyx* (500 mg of ground root) was extracted twice with 25 mL of the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The extracts were combined, concentrated and dried under low vacuum. Identification of chemical components in each extract was performed by HPLC using a PhotoDiode Array detector (HPLC/PDA) and a 250 mm×4.6 mm C18 column. The chemical components were quantified based on retention time and PDA data using baicalein, baicalin, scutellarein, and wogonin as standards. The results are set forth in Table 9.

TABLE 9

Quantification of Free-B-Ring Flavonoids Extracted from *S. orthocalyx*

| Extraction Solvent | Weight of Extract | % Extractible from BioMass | Total amount of Flavonoids | % Flavonoids in Extract |
|---|---|---|---|---|
| 100% water | 96 mg | 19.2% | 0.02 mg | 0.20% |
| Water:methanol (80:20) | 138.3 mg | 27.7% | 0.38 mg | 0.38% |
| Water:methanol (60:40) | 169.5 mg | 33.9% | 0.78 mg | 8.39% |
| Water:methanol (40:60) | 142.2 mg | 28.4% | 1.14 mg | 11.26% |
| Water:methanol (20:80) | 104.5 mg | 20.9% | 0.94 mg | 7.99% |
| 100% methanol | 57.5 mg | 11.5% | 0.99 mg | 10.42% |
| methanol:THF (80:20) | 59.6 mg | 11.9% | 0.89 mg | 8.76% |
| methanol:THF (60:40) | 58.8 mg | 11.8% | 1.10 mg | 10.71% |

*S. baicalensis* (1000 mg of ground root) was extracted twice using 50 mL of a mixture of methanol and water as follows: (1) 100% water, (2) 70:30 water:methanol, (3) 50:50 water:methanol, (4) 30:70 water:methanol, (5) 100% methanol. The extracts were combined, concentrated and dried under low vacuum. Identification of the chemical components was performed by HPLC using a PhotoDiode Array detector (HPLC/PDA), and a 250 mm×4.6 mm C18 column. The chemical components in each extract were quantified based on retention time and PDA data using baicalein, baicalin, scutellarein, and wogonin standards. The results are set forth in Table 10.

TABLE 10

Quantification of Free-B-Ring Flavonoids Extracted from *S. baicalensis*

| Extraction Solvent | Weight of Extract | % Extractible from BioMass | Total amount of Flavonoids | % Flavonoids in Extract |
|---|---|---|---|---|
| 100% water | 277.5 mg | 27.8% | 1 mg | 0.09% |
| Water:methanol (70:30) | 338.6 mg | 33.9% | 1.19 mg | 11.48% |
| Water:methanol (50:50) | 304.3 mg | 30.4% | 1.99 mg | 18.93% |
| Water:methanol (30:70) | 293.9 mg | 29.4% | 2.29 mg | 19.61% |
| 100% methanol | 204.2 mg | 20.4% | 2.73 mg | 24.51% |

Higher purity Free-B-Ring flavonoids can be obtained by recrystallization of extracts having a Free-B-Ring flavonoid content of between 8-15% using alcohol/water as a recrystallization solvent. It may be necessary to decolorize prior to recrystallization by adding active charcoal or other decolorization agent to a heated saturated solution of the extract. The Free-B-Ring flavonoids crystallized upon cooling. The crystals were filtered, dried and ground into a fine powder. Recrystallization can be repeated as necessary to achieve the desired level of purity (60%-100% of Free-B-Ring flavonoids).

Example 9

Preparation of a Formulation with a Standardized Free-B-Ring Flavonoid Extract from the Roots of *S. baicalensis* and a Standardized Flavan Extract from the Bark of *A. catechu*

A novel composition of matter, referred to herein as UP676 was formulated using two standardized extracts isolated from *Acacia* and *Scutellaria*, respectively, together with one or more excipients. A general example for preparing such a composition is set forth below. The *Acacia* extract used in this example contained >80% total flavans, as catechin and epicatechin, and the *Scutellaria* extract contained >80% Free-B-Ring flavonoids, which was primarily baicalin. The *Scutellaria* extract also contained other minor amounts of Free-B-Ring flavonoids as set forth in Table 11. One or more excipients/preservatives was also added to the composition of matter. The ratio of flavans and Free-B-Ring flavonoids can be adjusted based on the indications and the specific requirements with respect to inhibition of COX vs. LO, requirements of skin penetration, and potency requirements of the product, such as duration of potency required, etc. The quantity of the excipients can be adjusted based on the actual active content of each ingredient. A blending table for each individual batch of product must be generated based on the product specification and QC results for individual batch of ingredients. Additional amounts of active ingredients in the range of 2-5% are recommended to meet the product specification.

Figure 10:
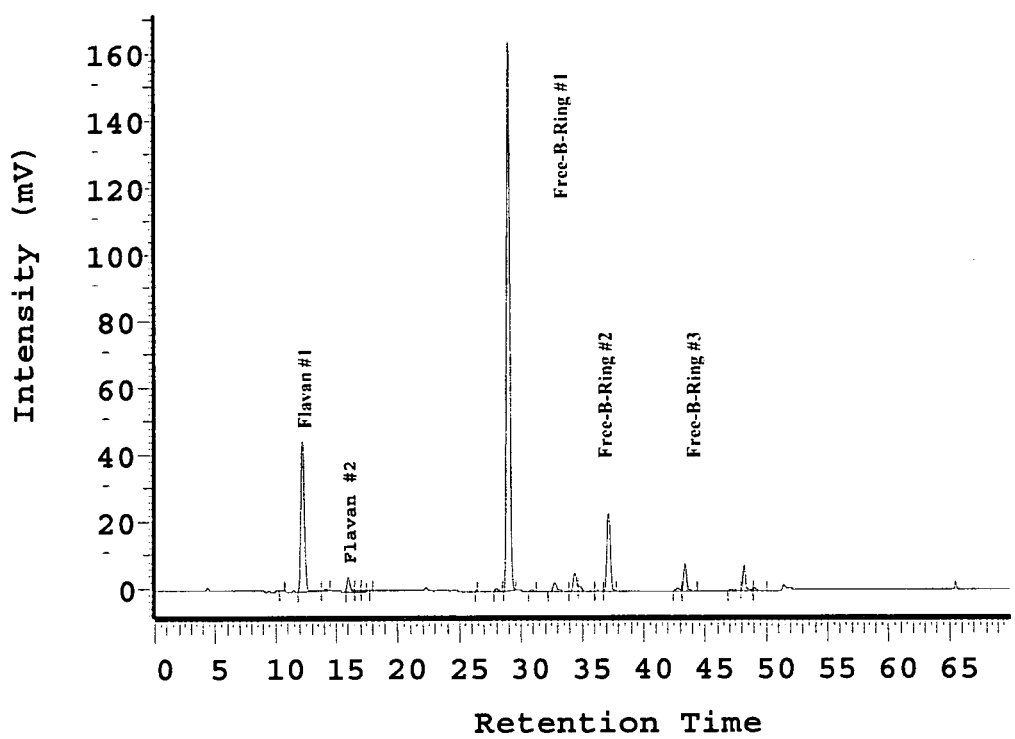
FIG. 10 illustrates the High Pressure Liquid Chromatography (HPLC) chromatogram of a typical formulation comprised of a mixture of Free-B-Ring flavonoids isolated from the roots of S. baicalensis and flavans isolated from the bark of A. catechu in a ratio of 80:20 carried out under the conditions as described in Example 9.

*S. baicalensis* root extract (38.5 kg) (lot # RM052302-01) having a Free-B-Ring flavonoid content of 82.2% (baicalin); *Acacia catechu* bark extract (6.9 kg) (lot # RM052902-01) with total flavan content of 80.4%; and excipient (5.0 kg of Candex) were combined to provide a UP676 formulation (50.4 kg) having a blending ratio of 85:15 by weight of the active Free-B-Ring flavonoids and flavans. Table 11 provides the quantification of the active Free-B-Ring flavonoids and flavans of this specific batch of UP676 (Lot#G 1702-COX-2), determined using the methods provided in Examples 6 and 8. With reference to Table 11, this specific batch of UP676 contains 86% total active ingredients, including 75.7% Free-B-Ring flavonoids and 10.3% flavans. FIG. 10 illustrates the HPLC chromatogram of a representative UP676 sample, which had a blending ratio of 80:20 by weight of the active Free-B-Ring flavonoids and flavans.

TABLE 11

Free-B-Ring Flavonoid and Flavan Content of a UP676 Formulation

| Active Components | % Content |
|---|---|
| 1. Flavonoids | |
|   a. Baicalin | 62.5% |
|   b. Minor Flavonoids | |
|     i. Wogonin-7-glucuronide | 6.7% |
|     ii. Oroxylin A 7-glucuronide | 2.0% |
|     iii. Baicalein | 1.5% |
|     iv. Wogonin | 1.1% |
|     v. Chrysin-7-glucuronide | 0.8% |
|     vi. 5-Methyl-wogonin-7-glucuronide | 0.5% |
|     vii. Scutellarin | 0.3% |
|     viii. Norwogonin | 0.3% |
|     ix. Chrysin | <0.2% |
|     x. Oroxylin A | <0.2% |
|   c. Total Free-B-ring Flavonoids | 75.7% |

TABLE 11-continued

Free-B-Ring Flavonoid and Flavan Content of a UP676 Formulation

| Active Components | % Content |
|---|---|
| 2. Flavans | |
| a. Catechin | 9.9% |
| b. Epicatechin | 0.4% |
| c. Subtotal Flavans | 10.3% |
| 3. Total Active Ingredients | 86% |

Using the same approach, the following batches of UP676 were prepared using a combination of a standardized Free-B-Ring flavonoid extract from *S. baicalensis* roots and a standardized flavan extract from *Acacia catechu* bark having a blending ratio of 12:88 and 15:85, respectively.

*S. baicalensis* root extract (58.0 g) (lot # RM021203-01) having a Free-B-Ring flavonoid content of 87.9% (as baicalin) and *Acacia catechu* bark extract (442.0 g) (lot # RM050603-01) with total flavan content of 84.9% were blended to provide a UP676 composition (500 g, lot#QJ205-19) having a blending ratio of 12:88 by weight. Utilizing the methods provided in Examples 6 and 8, the Free-B-Ring flavonoid content of (baicalin) was 9.65% and flavan content (total catechin and epicatechin) was 73.2% in this specific batch of UP676 (lot#QJ205-19).

*S. baicalensis* root extract (300 g) (lot # RM060403-01) having a Free-B-Ring flavonoid content of 82.9% (as baicalin) and *Acacia catechu* bark extract (1700 g) (lot # RM050603-01) with total flavan content of 90.8% were blended to provide a UP676 composition (2000 g, lot#A1904) having a blending ratio of 15:85 by weight. Utilizing the methods provided in Examples 6 and 8, the Free-B-Ring flavonoid content (baicalin) was 15.6% and flavan content (total catechin and epicatechin) was 75.0% in this specific batch of UP676 (lot#A1904).

Example 10

Measurements of Dose Response and $IC_{50}$ Values of 5-LO Enzyme Inhibition from a Formulation of UP676

A UP676 formulation (80:20) was prepared as described in Example 9 using a combination of a standardized Free-B-Ring flavonoid extract from *S. baicalensis* roots and a standardized flavan extract from *A. catechu* bark with a blending ratio of 80:20. The sample was titrated in tissue culture media containing THP-1 or HT-29 cells; monocyte cell lines that express COX-1, COX-2 and 5-LOX. A competitive ELISA for Leukotriene B4 (LTB4; Neogen, Inc., Cat#406110) was used to assess the effect of this UP676 formulation on newly synthesized levels of LTB4 present in each cell line as a measure UP676's inhibitory effect on the 5-LOX pathway. The assay was performed in duplicate by adding 160,000 to 180,000 cells per well in 6-well plates. The UP676 formulation was added to the THP-1 cultures at 3, 10, 30 and 100 μg/mL and incubated overnight (~12-15 hrs) at 37° C. with 5% $CO_2$ in a humidified environment. The results are set forth in FIG. 11, which shows that the production of newly LPS-induced LTB4 was almost completely inhibited by the addition of UP676 to the THP-1 cultures between 3 and 10 μg/mL.

UP676 and ibuprofen, another known 5-LOX inhibitor, were added to the HT-29 cells at 3 μg/mL and incubated 48 hrs at 37° C. with 5% $CO_2$ in a humidified environment. Each treated cell line was then harvested by centrifugation and disrupted by gentle dounce homogenization lysis in physiological buffers. As shown in FIG. 12, UP676 inhibited generation of 80% of the newly synthesized LTB4 in HT-29 cells. Ibuprofen only showed a 20% reduction in the amount of LTB4 over the same time period.

Example 11

UP676 down Regulated Gene Expression of Pro-Inflammatory Cytokines and Other Proteins Related to Inflammation at the mRNA Level Peripheral blood mononuclear cell (PBMC) is an established cell model for inflammation related disease. PBMCs from 3 healthy human subjects were stimulated with 10 ng/mL of lipopolysaccharide (LPS) both without and in the presence of various concentrations of UP676 (0, 10, 30 and 100 μg/mL). The cells were incubated at 37° C. with 5% $CO_2$ for 18 hrs before harvesting for RNA purification. RNA was prepared with the Qiagen RNeasy Kit and cDNA was synthesized with the ABI cDNA Archive kit. Real time quantitative-PCR assays were performed with an ABI Prism Sequence Detector. Either the 18S rRNA gene or the cyclophilin A gene was used as internal controls for normalization. A summary of the data derived from the three experiments is set forth in Table 12. On average, suppression of the gene expression of il-1β, tnfα and il-6 was 45-fold, 3-fold and 27-fold, respectively. Additionally, more than a 10-fold suppression of pparγ and a 2-fold suppression of nfκb mRNA by UP676 was detected at 18 hours post-stimulation with LPS in PBMCs.

TABLE 12

UP676 Gene Suppression in PBMCs (the numbers represent fold change of mRNA levels between the samples treated with 100 μg/mL and 0 μg/mL UP676)

| Gene | Subject #1 | Subject #2 | Subject #3 | Average |
|---|---|---|---|---|
| cox1 | 3 | −3 | −5 | −0.8 |
| cox2 | −71 | −84 | −35 | −63 |
| il-1β | −108 | −11 | −16 | −45 |
| tnfα | −6 | −1.5 | −2.5 | −3.3 |
| il-6 | nd | −40 | −34 | −27 |
| pparγ | nd | −7 | −13 | −10 |
| nfκb | −2.7 | −2.2 | −1.6 | −2.2 |

Example 12

Evaluation of the Efficacy of UP676 with In Vivo Mouse Ear Swelling Model

Figure 13:
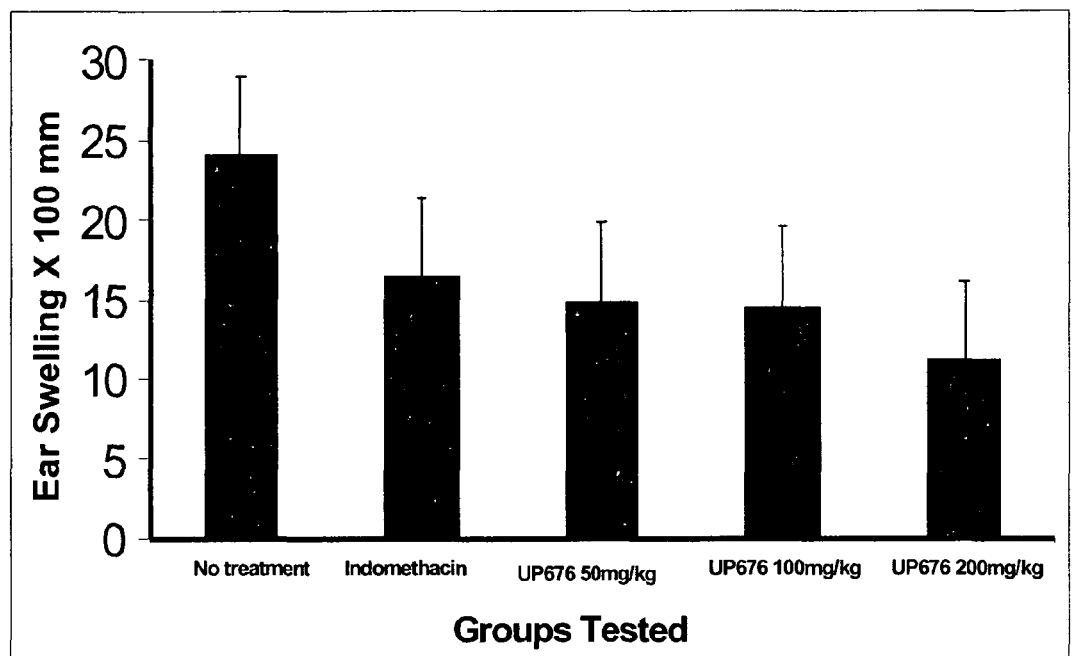
FIG. 13 illustrates graphically ear-swelling data as a measure of inhibition of inflammation as described in Example 12. UP676 produced through the combination of standardized extracts of Free-B-Ring flavonoids isolated from the roots of *S. baicalensis* and flavans isolated from the bark of *A. catechu* in a ratio of 80:20 was compared to untreated mice and mice given indomethacin (1.5 mg/kg) via oral gavage. The data is presented as the difference in micron measurement of the untreated vs. the treated ear lobe for each mouse.

A UP676 formulation was prepared using a combination of a standardized Free-B-Ring flavonoid extract from *S. baicalensis* roots and a standardized flavan extract from *Acacia catechu* bark with a blending ratio of 80:20 as described in Example 9. To test whether this composition could be used to treat inflammation in vivo, the composition was administered by oral gavage to 4-5 week old ICR mice (Harlan Labs) one day before treatment of their ears with arachidonic acid (AA). Test mice were fed dose equivalents of 50, 100 and 200 mg/kg of UP676 suspended in olive oil while control mice were fed only olive oil. The following day, 20 μL of 330 mM AA in 95% alcohol was applied to one ear of each mouse, while alcohol was applied to the other ear as a control. Mice treated with UP676 showed a measurable dose response that tracked with increasing doses of UP676, as demonstrated in FIG. 13. With reference to FIG. 13, the 200 mg/kg dose reduces swelling by over 50% as compared to the "No treatment" control. The 50 mg/kg dose of UP676 was as effective as the 50 mg/kg dose of another strong anti-inflammatory, indomethacin.

Example 13

Evaluation of the Efficacy of UP676 in Preventing and Treating Damage Resulting from Exposure of Skin to UV Radiation Six groups of hairless female mice (five mice per group) (Strain SKH-1, Harlan Labs) were irradiated, while anesthetized, for three minutes on three consecutive days with 0.626 mW/cm$^2$ to test the effectiveness of the UP676 formulation in preventing and treating damage resulting from exposure of skin to UV radiation. The UP676 formulation was prepared using a combination of a standardized Free-B-Ring flavonoid extract from *Scutellaria baicalensis* roots and a standardized flavan extract from *Acacia catechu* bark with a blending ratio of 80:20 as described in Example 9. The six treatment groups were as follows:

| Group # | |
|---|---|
| 1 | Control group: no treatment before or after UV irradiation |
| 2 | Positive control: treated with a topical application of Sooth-A-Caine (Banana Boat) after UV irradiation |
| 3 | UP676 Treatment B-1: treated with topical application of 1 mg/mL UP676 in water before UV irradiation |
| 4 | UP676 Treatment A-1: treated with topical application of 1 mg/mL UP676 in water after UV irradiation |
| 5 | UP676 Treatment B-2: treated with topical application of 5 mg/mL UP676 in water before UV irradiation |
| 6 | UP676 Treatment A-2: treated with topical application of 5 mg/mL UP676 in water after UV irradiation |

After three days of UV exposure and treatment, the mice were scored on level of erythema (redness) using the following scale: 0—no visible erythema; 1—very slight erythema; 2—well defined erythema; 3—severe erythema; and 4—tumor formation. Erythema was scored by eye for each group. The results are set forth in FIG. 14. With reference to FIG. 14 it can be seen that the control group (Group 1) had severe redness on day 3 (72 hours after the three day exposure to UV radiation). The Sooth-a-caine group also had maximum redness on day 3 (Group 2). The redness for the UP676 treated groups (Groups 3-6) never exceeded a score of 2. These scores, though subjective, show that UP676 is effective in both preventing and treating UV caused skin erythema.

Photographs of representative mice on day four clearly demonstrate differences between the control group, the Sooth-a-cain™ treated groups and the UP676 treated groups (data not shown). The control group and Sooth-a-cain™ treated animals exhibited very extensive patterns and redness of erythema compared to the animals treated with the UP676 formulation both before and after UV exposure. The animals treated before UV irradiation with 5 mg/mL UP676 exhibited the least amount of erythema as compared to all of the other animals.

Example 14

Formulation of the UP676 Composition into a Cream

UP676 (0.5% by weight of UP676) (lot#A1904 as described in Example 9) was formulated as a cream as illustrated in the following procedure and in Table 13.

UP676 (Lot#A1904) was dissolved in water at room temperature and homogenized with a blender until it was fully dispersed in solution (approximately 5 minutes). At room temperature and without stirring or agitating the solution, Ultrez-21 carbomer was added by sprinkling onto the surface of the solution and allowing it to fully wet (no white areas visible) and fall into the solution. With gentle stirring, the solution was then heated to 40° C. and glycerin was added (Part A). The mixture was then stirred for an additional 5 minutes. The remaining components (Part B) were weighed and heated to 40° C. while mixing. At 40° C., the remaining components (Part B) were added to Part A and the resulting composition was mixed well until homogenous (approximately 5 minutes). The emulsion was cooled to 30° C. and the pH was adjusted to approximately 5.5 (5.3 to 5.7) by titrating with neutralizer while stirring with a stir bar and/or spatula. The emulsion became highly viscous due to neutralization-induced conformational change of the carbomer. The emulsion eventually achieved a suitable viscosity for an emulsion cream. The emulsion cream was then mixed until uniform after which it was poured into a clean storage vessel and stored at 2° C. to 8° C. for one month.

TABLE 13

Ingredient list for a 0.5% UP676 Cream

| Phase | Ingredient | % (w/w) | Weight (g) |
|---|---|---|---|
| Aqueous | Water, Purified | 85.00 | 1275.0 |
| | UP676 (Lot#A1904) | 0.50 | 7.5 |
| | Ultrez 21 Carbomer | 0.50 | 7.5 |
| | Glycerin | 8.00 | 120.0 |
| Oil | PEG-7 Glyceryl Cocoate | 3.00 | 45.0 |
| | Caprylic/Capric Triglyceride | 2.67 | 40.0 |
| PH Neutralizer | Sodium Hydroxide (18% w/v), Molecular Biology Grade | 0.00 | 0.0 |
| SUM | 7 Ingredients | 99.7 | 1495.0 |

Example 15

Evaluation of the Stability of Catechin in Solution

Pure catechin was dissolved in 70% MeOH in water to a final concentration of 0.05% (W/V) after mixing with the solutions detailed below. A total of 6 different conditions (not including control solution) were chosen for this stability investigation at 45° C. Aqueous $K_2HPO_4$ (0.5 M) or $KH_2PO_4$ (0.5 M) was utilized to make buffered solutions at pH 5 or 8, respectively. $H_2O_2$, $SnCl_2$, $FeCl_3$ or EDTA was added to the catechin solution to a concentration of 0.6% $H_2O_2$, or 0.05% $SnCl_2$, or 0.05% $FeCl_3$ or 0.05% EDTA, respectively. All seven solutions were stored in sealed bottles at 45° C. Each sample was tested for catechin content by HPLC as described in the Example 6 at day 0, 1, 3, 6, 8, 10, 13, 20, and 28. The results are set forth in FIG. 15.

The following preservatives: BHA, BHT, diammonium citrate (DAC), $H_2O_2$, propyl gallate (PG), sodium gluconate (SG), and sodium bisulfate/metabisulfite (SBS), were added into a buffered (pH 7.5) 0.05% catechin MeOH/$H_2O$ solution to yield a concentration of 0.05%. All eight solutions were stored in sealed bottles at 45° C. Each sample was tested by HPLC as described in Example 6 for catechin content at day 0, 1, 3, 6, 8, 10, 13, 20, and 28. The results are set forth in FIG. 16.

Example 16

Evaluation of the Bioavailability of Baicalin in UP676 after Oral Administration This clinical study was a single-center, open-label study in which ten healthy subjects (n=10, 6 female and 4 mate) were recruited to participate. The subjects fasted overnight and reported to the clinical trial center at 8:00 a.m. the next morning. Each subject received a dose of 300 mg UP676 prepared as described in Example 9 immediately following a baseline venipuncture. Follow-up plasma samples were collected at ½, 1, 2, 4 and 8 hours. Additional samples were collected at 24 hours on day two and on the seventh day. Each plasma specimen was processed by collecting the blood into heparin-containing tubes. The blood was then centrifuged at 2,500 rpm for 10 minutes. Supernatant from each tube was split, transferred into transfer tubes, and stored at −70° C. for analysis following the final collections before determination of Free-B-ring flavonoid levels. This analysis was undertaken to determine: (i) area under the curve (AUC) for absorption and clearance of Free-B-Ring flavonoids; (ii) maximum plasma concentration ($C_{max}$) of Free-B-Ring flavonoids; (iii) time to maximum plasma concentration ($T_{max}$) for Free-B-Ring flavonoids; (iv) plasma elimination half-life ($T_{1/2}$) of Free-B-Ring flavonoids; and, (v) 24 hour urinary clearance $A_U^{24Hr}$.

Preliminary investigation of several test aliquots of the sera by HPLC revealed that the Free-B-Ring flavonoids were below the detection limit (<4 μg/mL) due to conjugation via glucuronidation and sulfation. Therefore, the sera was digested with β-glucuronidase at 2,000 u/mL and sulfatase at 170 u/mL to allow conversion of all conjugated Free-B-Ring flavonoids into the aglycone molecule baicalein. The total baicalein metabolites were then by HPLC using pure baicalein as a standard. Ascorbic acid was added to prevent oxidation of the flavonoids during the 7 hour digestion at 37° C. and subsequent HPLC analysis.

After β-glucuronidase and sulfatase digestion of the plasma, the flavonoid was extracted with ethyl acetate and then promptly evaporated to dryness with a nitrogen stream and gentle heating (35° C.) before HPLC analysis. An 80:20 methanol:tetrahydrofuran solution containing 1 mg/mL ascorbic acid buffer was used to reconstitute the sample. Quantification of baicalein was achieved by reverse-phase chromatography using an isocratic gradient of 0.1% phosphoric acid (v/v) (buffer A) and acetonitrile (buffer B) at a flow rate of 1 mL/min with pure baicalein standard material for mass calibration and retention time identification. Detection of eluted material was monitored using an inline UV detector measuring at 275 nm.

The results are set forth in FIG. 17. With reference to FIG. 17, the data shown in bold represents the points used to calculate the plasma clearance of baicalein. When logarithmically transformed and graphed for all subjects, these data represented a linear function with respect to time (data not shown). There was individual variation seen from subject to subject. Table 14 shows the maximal values found for baicalein concentration ($C_{max}$, μg/mL) and time ($T_{max}$, hour) which were observed for each subject. The data shows that for most subjects, the maximum concentration was achieved between 4 and 8 hours after the initial dose. The average $C_{max}$ was 0.93 μg/mL (% RSD=84.9) and the average $T_{max}$ was approximately 5.8 hours (% RSD=43.4). Based on this data, the average for absorption and clearance was calculated and plotted for the entire study group (FIG. 17).

TABLE 14

Maximal values of baicalein concentration ($C_{max}$, μg/mL) and time ($T_{max}$, hour) observed for each subject.

| | A | B | C | D | E | F | G | H | I | J |
|---|---|---|---|---|---|---|---|---|---|---|
| $C_{max}$ (μg/mL) | 1.1 | 0.80 | 0.38 | 0.58 | 0.44 | 2.8 | 0.88 | 0.47 | 0.14 | 0.26 |
| $T_{max}$ (hour) | 2.0 | 8.0 | 4.0 | 8.0 | 8.0 | 4.0 | 8.0 | 4.0 | 8.0 | 8.0 |

Example 17

Evaluation of a UP676 Cream for Irritation and Induction of Contact Sensitization by Repetitive Application to Human Skin The UP676 was tested on human skin using an adaptation of the Draize Patch Test (Marzulli and Maibach (1977) Contact Allergy: Predictive Testing in Humans. In Advances in Modern Toxicology, Dermatotoxicology and Pharmacology. Eds. Marzulli, F. N and Maibach, H. I. 4, 353-372). The test sites were located on the upper arm or the paraspinal region of the back. Each test article had an induction site and a challenge site. The induction site was comprised of two sub-sites: an original-site and a move-site. Patches, containing 0.2 mL of UP676 cream/patch prepared as described in Example 14, were applied repeatedly to the original-site unless a sufficiently strong irritation reaction developed, requiring the patch to be applied to the move-site. Patches were applied by a clinical research institute and were removed and discarded by the subjects approximately 24 or 48/72 hours later. In the induction phase, repetitive application of the test article to the same site on the skin and a total of 9 induction patches were applied within a 4-week period. The rest period was 10 to 21 days between application of the last induction patch and application of the challenge patch. During this time no test article or any other material was applied to the test area. At the challenge phase, the test article was applied to a naive site on the opposite side of the body and discarded by the subjects approximately 24 or 48 hours later.

Skin responses to each patch application were examined and graded under light supplied by a 100-watt incandescent blue bulb according to the designated scoring scale. In instances where a strong irritation reaction warranted application of the test article to the move-site, residual scores were be recorded through the end of induction (or until resolved if reactions persist after induction is completed) for all previously exposed sites. All skin reactions were recorded. During the challenge phase, skin responses were evaluated approximately 48 and 72 or 96 hours after patch application. Conclusions, with regard to induced sensitivity, were derived primarily from the challenge evaluations.

The two UP676 creams prepared in the Example 14 at 0.5% and 1.5% UP676 concentrations were evaluated according to the above protocol. A total of 120 subjects were recruited for each group. Ninety-seven subjects completed the study for the 0.5% UP676 group and 101 subjects completed the study for 1.5% UP676 group. There was no evidence of sensitization reaction for either the 0.5% and 1.5% UP676 creams. For the 0.5% UP676, during induction, sixteen subjects exhibited occasional occurrences of slight to mild erythema (scores of + and/or 1). At challenge, four subjects exhibited slight to mild erythema at 48 hours that cleared by 96 hours. For 1.5% UP676, during induction, twenty-six subjects exhibited occasional occurrences of slight to mild erythema (scores of + and/or 1). At challenge, one subjects exhibited slight to mild erythema at 48 hours that cleared by 96 hours.

This study demonstrates that UP676 is a safe ingredient that can be applied topically to human skin at an efficacious concentration without causing irritation or sensitization.

What is claimed is:

1. An oral care composition, comprising:
a mixture of a *Scutellaria* extract enriched for baicalin and an *Acacia* or *Uncaria* extract enriched for catechin or epicatechin or both; and a polymeric polycarboxylate;
wherein the composition is in the form of a toothpaste, gel, cream, mouthwash, chewing gum, tincture or drink.

2. The composition according to claim 1 wherein the composition further comprises a solubilizing agent and an efficacy-enhancing agent.

3. The composition according to claim 2, wherein the efficacy-enhancing agent is selected from an anionic polymer or co-polymer comprising a delivery-enhancing group and a retention-enhancing group, wherein the delivery-enhancing group enhances delivery of a flavonoid and a flavan to oral tissue and the retention-enhancing group enhances retention of the flavonoid and the flavan by oral tissue.

4. The composition according to claim 2, wherein the solubilizing agent is selected from an ether, a glycol, a fat, an oil, a lipid, a surfactant, an alcohol, a humectant, and mixtures thereof.

5. The composition according to claim 1, further comprising an oral care active agent that is selected from the group consisting of: an antibacterial agent, an antimicrobial agent, an anti-caries agent, an anti-tartar agent, an anti-attachment agent, a biofilm disruption agent, an anti-inflammatory agent, an antibiotic, and mixtures thereof.

6. The composition according to claim 1, further comprising an oral care active agent that comprises a non-ionic compound.

7. The composition according to claim 1, further comprising an oral care active agent that comprises an active compound selected from the group consisting of: benzethonium chloride, octenidine, hexetidine, hexamidine, cetyl pyridinium chloride, chlorhexidine, alexidine, $N^{\alpha}$-cocoyl-L-arginine methyl ester, $N^{\alpha}$-cocoyl-L-arginine ethyl ester, $N^{\alpha}$-cocoyl-L-arginine propyl ester, $N^{\alpha}$-stearoyl-L-arginine methyl ester, $N^{\alpha}$-stearoyl-L-arginine ethyl ester, $N^{\alpha}$-Lauroyl arginine ethyl ester, 2',4,4'-trichloro-2-hydroxy-diphenyl ether (triclosan), stannous ion source, fluoride ion source, zinc ion source, salts and mixtures thereof.

8. An oral care composition, comprising:
a mixture of a *Scutellaria* extract enriched for free-B-ring flavonoids containing primarily baicalin and an *Acacia* or *Uncaria* extract enriched for flavans containing primarily catechin or epicatechin or both; and a polymeric polycarboxylate;
wherein the composition is in the form of a toothpaste, gel, cream, mouthwash, chewing gum, tincture or drink, and wherein the free-B-ring flavonoids and the flavans are present in an amount of about 0.05% to about 25% by weight of the composition.

9. The composition according to claim 8, wherein said mixture of free-B-ring flavonoids and flavans is formulated as a toothpaste in an amount of 0.1% to 5% by weight of the composition.

10. The composition according to claim 8, wherein said mixture of free-B-ring flavonoids and flavans is formulated as a mouthwash in an amount of 0.2% to 1% by weight of the composition.

11. The composition according to claim 8, wherein said mixture of free-B-ring flavonoids and flavans is formulated as an emulsion gel or cream in an amount of 0.5 to 5% by weight of the composition.

* * * * *